(12) United States Patent
Kang et al.

(10) Patent No.: US 7,867,730 B2
(45) Date of Patent: Jan. 11, 2011

(54) HANSENULA POLYMORPHA GENE CODING FOR α 1,6-MANNOSYLTRANSFERASE AND PROCESS FOR THE PRODUCTION OF RECOMBINANT GLYCOPROTEINS WITH HANSENULA POLYMORPHA MUTANT STRAIN DEFICIENT IN THE SAME GENE

(75) Inventors: Hyun-Ah Kang, Daejeon (KR); Moo-Woong Kim, Daejeon (KR); Sang-Ki Rhee, Seoul (KR); Joo Hyung Heo, Daejeon (KR)

(73) Assignee: Korea Research Institute of Biosciences and Biotechnology, Inc., Daejeon (KR)

( * ) Notice: Subject to any disclaimer, the term of this patent is extended or adjusted under 35 U.S.C. 154(b) by 313 days.

(21) Appl. No.: 10/587,956

(22) PCT Filed: Jul. 21, 2004

(86) PCT No.: PCT/KR2004/001819

§ 371 (c)(1),
(2), (4) Date: Oct. 5, 2007

(87) PCT Pub. No.: WO2005/073382

PCT Pub. Date: Aug. 11, 2005

(65) Prior Publication Data

US 2008/0305525 A1  Dec. 11, 2008

(30) Foreign Application Priority Data

Jan. 30, 2004  (KR) .................. 10-2004-0006352

(51) Int. Cl.
C12P 21/06 (2006.01)
C12P 19/00 (2006.01)
C12P 19/04 (2006.01)
C12N 9/10 (2006.01)
C12N 1/00 (2006.01)
C12N 15/00 (2006.01)
C12Q 1/48 (2006.01)
C07H 21/04 (2006.01)
C07K 1/00 (2006.01)

(52) U.S. Cl. .................. 435/69.1; 435/193; 435/15; 435/254.23; 435/254.11; 435/320.1; 435/72; 435/101; 536/23.1; 536/23.2; 530/395

(58) Field of Classification Search .............. 435/69.1, 435/193, 15, 254.23, 254.11, 320.1, 72, 10; 536/23.1, 23.2; 530/395
See application file for complete search history.

(56) References Cited

FOREIGN PATENT DOCUMENTS

| EP | 1505149 A1 | 2/2005 |
|---|---|---|
| JP | 2007150780 A | 6/2007 |
| WO | WO 92/19741 A1 | 11/1992 |
| WO | WO 02/00856 A2 | 1/2002 |
| WO | WO 02/00879 A2 | 1/2002 |
| WO | WO 2004/003205 A1 | 1/2004 |

OTHER PUBLICATIONS

Kim et al., Cloning and characterization of the *Hansenula polymorpha* homologue of *Saccharomyces cerevisiae* MNN9 gene. Yeast, 2001, vol. 18: 455-461.*
Guo et al., Protein tolerance to random amino acid change. PNAS., 2004, vol. 101 (25): 9205-9210.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol.,2001, vol. 183 (8): 2405-2410.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Kim et al., Functional characterization of the *Hansenula polymorpha* HOC1 . . . J. Biol. Chem., 2006, vol. 281 (10): 6261-6272.*
English Translation of Abstract; JP Patent Publication No. JP2007150780; Published: Jun. 14, 2007; Applicant: CB KK; (1 pg.).
Chiba, Yasunori, et al.; Production of Human Compatible High Mannose-type (Man5GlcNAc2) Sugar Chains in *Saccharomyces cerevisiae*; The Journal of Biological Chemistry (Oct. 9, 1998); vol. 273, No. 41, pp. 26298-26304.
Ballou, Clinton; "Isolation, Characterization, and Properties of *Saccharomyces cerevisiae* mnn Mutants with Noncondictional Protein Glycosylation Defects"; Methods Enzymol. (1990); pp. 440-441.
Choi, Byung-Kwon, et al.; Use of combinatorial genetic libraries to humanize N-linked glycosylation in the yeast *Pichia pastoris*; PNAS (Apr. 29, 2003); vol. 100, No. 9; pp. 5022-5027.
Nakanishi-Shindo, Yoko, et al.; Structure of the N-Linked Oligosaccharides That Show the Complete Loss of a-1,6-Polymannose Outer Chain from och1, och1, mnn1, and och1 mnn1 alg3 Mutants of *Saccharomyces cerevisiae*; The Journal of Biological Chemistry (Dec. 15, 1993); vol. 268, No. 35; pp. 26338-26345.

* cited by examiner

Primary Examiner—Ganapathirama Raghu
(74) Attorney, Agent, or Firm—Casimir Jones, S.C.

(57) ABSTRACT

Disclosed are a novel *Hansenula polymorpha* gene coding for α-1,6-mannosyltransferase initiating outer chain elongation, an *H. polymorpha* mutant strain having a deficiency in the gene, and a process for producing a recombinant glycoprotein using such a mutant strain.

11 Claims, 9 Drawing Sheets

Fig. 1
(SEQ ID NO: 1)

```
  -9  cggtgaagaatggtgtatttttaaatttcatgtcaataaccaatgtcccggtgctgaag
             M  V  Y  F  L  N  F  M  S  I  T  N  V  P  V  L  K
  52  cgcgcgcgactctacatggcgacgaatcgccggctggtggttgttcttgtggtgctgctg
         R  A  R  L  Y  M  A  T  N  R  R  L  V  V  V  L  V  V  L  L
 112  tactgggtggtccagaacgtttggacgtggagccctgggacgcgcgatttggcccaagtg
         Y  W  V  V  Q  N  V  W  T  W  S  P  G  T  R  D  L  A  Q  V
 172  gacgcgaagatcgaggccgagctaaactcgaatctacatactttggagcgcatttgcgc
         D  A  K  I  E  A  E  L  N  S  N  L  H  T  F  G  A  H  L  R
 232  cacttaaaccggcttccggcagagtcggccaccctgcgtgaaaaactcaccttctatttc
         H  L  N  R  L  P  A  E  S  A  T  L  R  E  K  L  T  F  Y  F
 282  ccatattatcctgaaaagcccgtgccgaaccagatctggcagacatggaaggtcgatctc
         P  Y  Y  P  E  K  P  V  P  N  Q  I  W  Q  T  W  K  V  D  L
 352  gaagacgacaacttccccaagcagtacagacggtttcagaagacgtgggtcgagaaaaat
         E  D  D  N  F  P  K  Q  Y  R  R  F  Q  K  T  W  V  E  K  N
 412  ccagactacgtgtaccacctgattccggactctgtgattgaggactttgtggcgagtttg
         P  D  Y  V  Y  H  L  I  P  D  S  V  I  E  D  F  V  A  S  L
 472  tacgcgaacgtgccggaggtggtcagagcgtaccagctgcttccgaaaaatatcatgaag
         Y  A  N  V  P  E  V  V  R  A  Y  Q  L  L  P  K  N  I  M  K
 532  gcggattttttccggtatttggtgatctacgcgcgcggaggcacctactcagacatggac
         A  D  F  F  R  Y  L  V  I  Y  A  R  G  G  T  Y  S  D  M  D
 592  acggtgtgtttaaagccgatcaaggactgggccacgtttgatcgcgacctgatccacgct
         T  V  C  L  K  P  I  K  D  W  A  T  F  D  R  D  L  I  H  A
 652  gccgacaataaggccgatctctcccagatagatccagaagcaagaaccacgcctgtgggg
         A  D  N  K  A  D  L  S  Q  I  D  P  E  A  R  T  T  P  V  G
 712  ctggtgattggcattgaggccgacccggacaggcccgactggcacgagtggttctcgcgc
         L  V  I  G  I  E  A  D  P  D  R  P  D  W  H  E  W  F  S  R
 772  agactgcagttctgccagtggacgatccaggcgaagccgggacacccgctgctgcgcgag
         R  L  Q  F  C  Q  W  T  I  Q  A  K  P  G  H  P  L  L  R  E
 832  ctgatcatccggatcgtggaggagacgttccgcaaacagcacatgggcgttttgaaaaga
         L  I  I  R  I  V  E  E  T  F  R  K  Q  H  M  G  V  L  K  R
 892  gtggaaggcaaggactcgggcgcagatatcatgcagtggacaggaccggggatatttaca
         V  E  G  K  D  S  G  A  D  I  M  Q  W  T  G  P  G  I  F  T
 952  gacactctgtttgattatctgaacaatgtggcgagcgacggcaagttgggcgacgggtac
         D  T  L  F  D  Y  L  N  N  V  A  S  D  G  K  L  G  D  G  Y
1012  ggcgtggggtcgttgtattggcgcaagcacggcaaatataagctgaaaaagacagaaatt
         G  V  G  S  L  Y  W  R  K  H  G  K  Y  K  L  K  K  T  E  I
1072  aacaagaataacgagccattgcattctgaggaccagcttatcaactggaggtcgctgacc
         N  K  N  N  E  P  L  H  S  E  D  Q  L  I  N  W  R  S  L  T
1132  aacatggacaagccaaagatcatgggggacgtaatggtgttaccaatcacgagctttagt
         N  M  D  K  P  K  I  M  G  D  V  M  V  L  P  I  T  S  F  S
1192  ccgaacgtggggcacatgggctcaaagagcagctcagataggctggcatttgtggagcat
         P  N  V  G  H  M  G  S  K  S  S  S  D  R  L  A  F  V  E  H
1252  ttattttctggcagctggaagccaaaaaacaaataggaaaaataaataattagctgcatt
         L  F  S  G  S  W  K  P  K  N  K  -
1312  ttagataattctcatgagcaggcacagaacg
```

Fig. 2

```
                                                                                     SEQ ID NO.:
Hp0ch2p    1 ------------------------------MVYFLNFMSITNVPVLKRAR YMATNRRLVVVLV   YWV    2
Hp0chlp    1 -------------------------------MSKASPYRGINSTSSTSPRFRRLS F GLL          15
Ca0chlp    1 ----------------------------MLQLREPQMWHKH KLAVLGIVVIFTTYF ISS          16
Pp0chlp    1 -------------------------------MAKAD G L YYNPHNPPRRYYFY AIFA           17
Sc0chlp    1 -------------------------------MSRKL H IATRKSKTIVVTV   YSL             18
Sp0chlp    1 ----MLRLRLRSIVIGAAIAGSILLLFNHGSIEGMEDLTEISMLEDY PEAANKDYVGQQEEEE  YDQP  19

Hp0ch2p   42 QN WTWSPGTPDLAQVDAKI AK N---SNLHTFGA LR----------HLNRLPAESATL   L  YFPY   2
Hp0chlp   32 GL LFKFSTSWSINTEDKIVSEY N----NFYKLNP FRG----------ANPYDAAVTA  LAKFFPY   15
Ca0chlp   35    SPTSTHKTEY SPKLQ AR LE N---SNWKELG NFQP--------NKKYSLPDESTL QQ  QFPY   16
Pp0chlp   30  V CVLYGPSQ LSSPR DY PLTL---RSLDLKTL AP---------SOLSPGTVEDML  PQL HFPY   17
Sc0chlp   29  FHLSNKRLLS FYPSKDDFKQT LPTTSHSQDIN KQI---------TVNKKKNQLHNL QL  AFFY    18
Sp0chlp   67  Y EEEEDPDLEAYLSD  ER EL KHSLEELDEENNY LHLRYSFSQLQDFDEENEAVHM VP D  E EV  19

Hp0ch2p  100 Y-PE E PNQIWQ TWK D LEDDNF  Q  R QF IV-E NPDDVYH   PDSVIEDF ASL AN--VPEV   2
Hp0chlp   87 DNSA  D KS IWQN WKWPSTE PDFD  R LVN KW NE---MPT YKYN   TDDEIL    RID KDT-VP V   15
Ca0chlp   94  E-RS  F KN IWQ TWKWGID KSFP  R LKQQ  EB-D NPDYKRY R LFKQCDL EQLYSQ--VP LA   16
Pp0chlp   88 P-SYE F FQH IWQ TWKRW SPSDSS FP N  DLGE IL-Q SPNYD FF  PDDAAWE  HHENER--VPEV    17
Sc0chlp   91 R-SOA   R OD WQ TWKWGAD KNFPSS  T OR   SGSYSPDW QYSL  SDDSIIPF EN  NAP--WRI    18
Sp0chlp  137 P-YHAD   PKL IWQ TSK DP-----FD EVMR  TRFW R-INH SWSHA   DD QSKA  ISS GDSS SK S 19

Hp0ch2p  166 RA  QLL KN I  KADFFRYL   ARGG Y  D T  CLKPI RD A  FD RD IHAADNK--------ADLSQI  2
Hp0chlp  153 BA  E LPNR I  DPAR YL  FLN GG Y DT DLQKR  TW FDSDRN GF-----------------     15
Ca0chlp  160 RA  P  PKS ILKADF FRYL LFARGG YY DT  GLKR  EQ  NSE  LEKRN-----------------      16
Pp0chlp  154 BA  HLL PE PILKADF FRYL LFARGG YD DT  DLKRI SW  FNET  GGVKN---------------      17
Sc0chlp  158   A  PL PG M ILKADF L RYL LFARGG Y DT  DLKPI SW  QNKSWLNNIIDLNKPIPYKNSKPSLL   18
Sp0chlp  200 QA A   D LP LKADFFRYL LLA GG Y  D TA PLRK HINN   PREYRKRN---------------          19

Hp0ch2p  228 DPEARTTPV  AVI GI EAD PD RPDWH   RD QFCQWTIQAKPGHP LRELI   IV  BTF---------    2
Hp0chlp  204 -----------WI  REDD I VE  KH MTPRIQFBQWTFKAKAKHPILRKLIA IV  TFQARRN-----       15
Ca0chlp  214 ------RS  GLV GI EAD PD RPDW A  WYARRIQFCQWTIQ KPGHP LRELIA  IL ITLT-------        16
Pp0chlp  208 ------NA GLVIGIEAD PD RPDWH  WYARRIQFCQWAIQ RRGHPALRELIV  VSTTL----------         17
Sc0chlp  228 SSDEISHQP GLVIGIEAD PD RDDWS  WYARRIQFCQWTIQAKPCHPILRELILN ATTLASVQNPGVPV  18
Sp0chlp  251 ---------IR W  GIRAD PD RPDWN  WYARR QFCQWTIAA PCH I WRL R IV BW---------           19

Hp0ch2p  289 -------------- Q  ME VL RRV GK DS----GAD INQWTGPGIFTDT  Y MN  ASD------    2
Hp0chlp  258 -------------DKLQ YYRDFR  RR--CASW INWTGPV  TDDILAH MS  PSPTIVDI   15
Ca0chlp  268 --------------H R Q L RKVLG  E----GDIM WTGPGIFTDI  F MN  LQS-----              16
Pp0chlp  262 --------------E SR YN MVE RR--GSA  DWTGPGIFTDI    TW  NTT-----                 17
Sc0chlp  298 SEMIDPRFEEDYNVNYRHR  R DETYRHSLE  NRNVDGSDIN WTGPGI  DII F YNN  LRYNSDIL  18
Sp0chlp  304 ------------------LHDSK RL SRNG  S-------  EWTGPGI TLA D Y NWQYGP-----   19

Hp0ch2p  331 ---GK GD GYGVGSLYWRHGKYKLKRTEINKNNEPLHSED------Q   N  SL DN   RPK  GDVIWL   2
Hp0chlp  307 DHQRD AGELYG----------------------------PETGEGD   W  FR G  PAEV   DDV  Y   15
Ca0chlp  310 ---PE FKNKKK--------------------------W-----AT   DW LFTG   QEIA DDVLWL   16
Pp0chlp  304 ---GHSGQGIGAGSAYYNALSLEERDALSARPNGEMLKERVPGKYAQQ  LWRQ  N  PSPK  DD L L   17
Sc0chlp  368 LINPM NKNDEEGSESATTPARDVDNDTLSKSTRKFYKKISESLOSSNS   RWEF  F IFKEV  DDVWL   18
Sp0chlp  341 ----------------------------------------FSVENI NL ELY  GDVLL   19

Hp0ch2p  392 PITSF SPNWG  MG   SSS  L  EHLFS GSWR PNK--------------------   2
Hp0chlp  348 P RASFREDK-----BNMCG YQYW HHF GGSWR  NGKGEIKPGMEGYEGEDPNEVEELRKNDVSKRDVIP   15
Ca0chlp  344 PITSFSPDW QMG  DSH QP  AYA HMFS GSWR  DGMPEMKQ-----------------   16
Pp0chlp  371 PITSFSPC  G  S ACDLNH  AY  HTF GSW       --------------------   17
Sc0chlp  438 PITSFSPDW QMG QQSSD   A  HMFS GSWK  DADKNAGHK-------------------   18
Sp0chlp  362 P T  SQCWG  MG   SPN P  AV QH RA GW  D--------------------   19

Hp0ch2p      --------------------    100%   2
Hp0chlp  413 GESKDVAPVKKLAKRCAYPYTPY 27.3%  15
Ca0chlp      --------------------    42.3%  16
Pp0chlp      --------------------    40.0%  17
Sc0chlp      --------------------    40.4%  18
Sp0chlp      --------------------    30.8%  19
```

Fig 3. Analysis of Sugar-chain structure of Hansenula polymorpha adding N-acetylglucosamine using Capillary electrophoresis (CE)
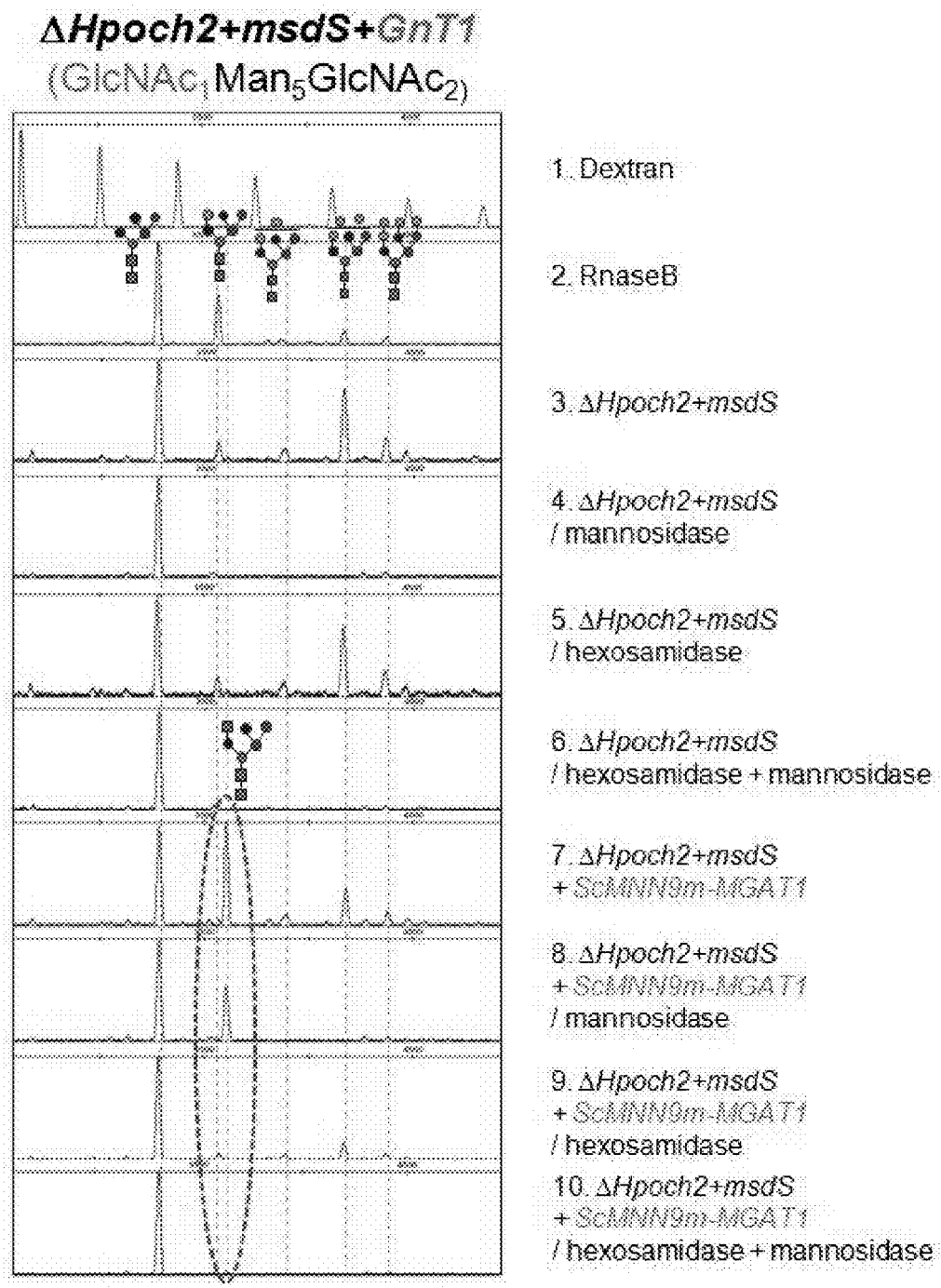

Fig. 6
A.
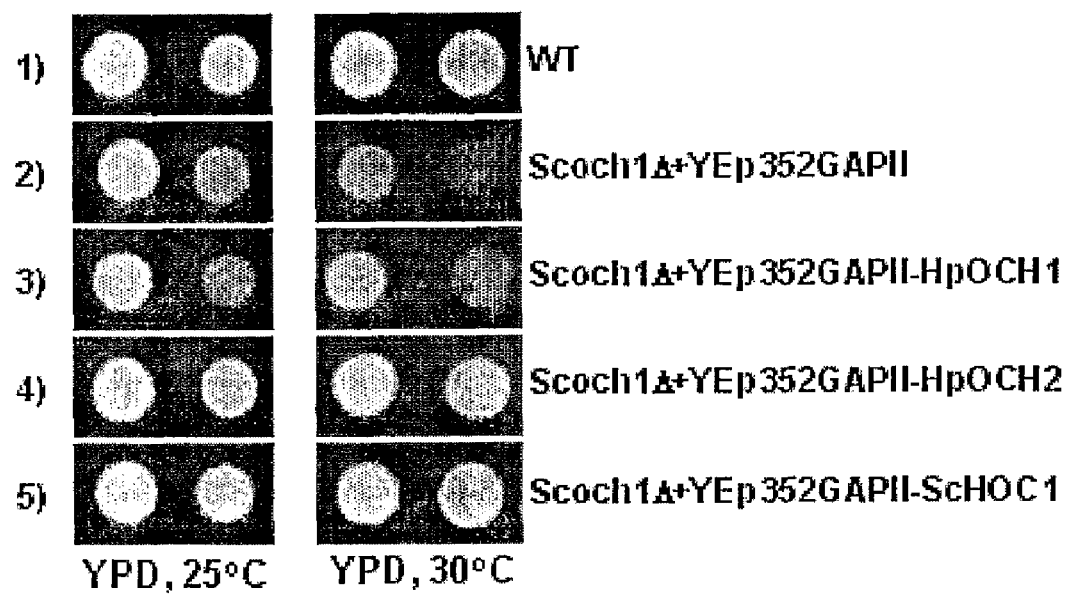
1) WT
2) Scoch1Δ+YEp352GAPII
3) Scoch1Δ+YEp352GAPII-HpOCH1
4) Scoch1Δ+YEp352GAPII-HpOCH2
5) Scoch1Δ+YEp352GAPII-ScHOC1
YPD, 25°C    YPD, 30°C
B.
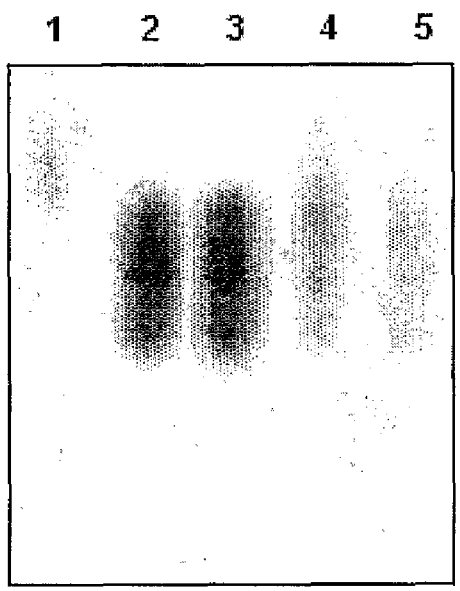

Fig. 9

| | ScHoclp | ScOchlp | HpOchlp | ORF379 | ORF168 | ORF288 | ORF580 | ORF100 | ORF576 |
|---|---|---|---|---|---|---|---|---|---|
| ScHoclp (396 aa) | | 20 | 21 | 40 | 23 | 18 | 19 | 18 | 17 |
| ScOchlp (480 aa) | 36 | | 22 | 24 | 37* | 21 | 18 | 17 | 15 |
| HpOchlp (435 aa) | 36 | 36 | | 19 | 22 | 22 | 32 | 21 | 19 |
| ORF379 (402 aa) | 63 | 40 | 34 | | 28 | 18 | 21 | 17 | 16 |
| ORF168 (428 aa) | 41 | 54* | 39 | 45 | | 21 | 21 | 20 | 17 |
| ORF288 (414 aa) | 35 | 36 | 40 | 34 | 40 | | 21 | 51 | 33 |
| ORF580 (362 aa) | 34 | 36 | 48 | 35 | 39 | 40 | | 20 | 19 |
| ORF100 (425 aa) | 34 | 33 | 37 | 33 | 36 | 66 | 38 | | 32 |
| ORF576 (369 aa) | 30 | 31 | 33 | 30 | 32 | 50 | 33 | 47 | |

Identity →

Similarity →

SEQUENCE LISTING

<160> NUMBER OF SEQ ID NOS: 19

<210> SEQ ID NO 1
<211> LENGTH: 1351
<212> TYPE: DNA
<213> ORGANISM: Hansenula polymorpha
<220> FEATURE:
<221> NAME/KEY: CDS
<222> LOCATION: (10)..(1293)

<400> SEQUENCE: 1

```
cggtgaaga atg gtg tat ttt tta aat ttc atg tca ata acc aat gtc ccg      51
         Met Val Tyr Phe Leu Asn Phe Met Ser Ile Thr Asn Val Pro
         1               5                   10 gtg ctg aag cgc gcg cga ctc tac atg gcg acg aat cgc cgg ctg gtg       99
Val Leu Lys Arg Ala Arg Leu Tyr Met Ala Thr Asn Arg Arg Leu Val
15                  20                  25                  30 gtt gtt ctt gtg gtg ctg ctg tac tgg gtg gtc cag aac gtt tgg acg      147
Val Val Leu Val Val Leu Leu Tyr Trp Val Val Gln Asn Val Trp Thr
                35                  40                  45 tgg agc cct ggg acg cgc gat ttg gcc caa gtg gac gcg aag atc gag      195
Trp Ser Pro Gly Thr Arg Asp Leu Ala Gln Val Asp Ala Lys Ile Glu
        50                  55                  60 gcc gag cta aac tcg aat cta cat act ttt gga gcg cat ttg cgc cac      243
Ala Glu Leu Asn Ser Asn Leu His Thr Phe Gly Ala His Leu Arg His
            65                  70                  75 tta aac cgg ctt ccg gca gag tcg gcc acc ctg cgt gaa aaa ctc acc      291
Leu Asn Arg Leu Pro Ala Glu Ser Ala Thr Leu Arg Glu Lys Leu Thr
    80                  85                  90 ttc tat ttc cca tat tat cct gaa aag ccc gtg ccg aac cag atc tgg      339
Phe Tyr Phe Pro Tyr Tyr Pro Glu Lys Pro Val Pro Asn Gln Ile Trp
95                  100                 105                 110 cag aca tgg aag gtc gat ctc gaa gac gac aac ttc ccc aag cag tac      387
Gln Thr Trp Lys Val Asp Leu Glu Asp Asp Asn Phe Pro Lys Gln Tyr
                115                 120                 125 aga cgg ttt cag aag acg tgg gtc gag aaa aat cca gac tac gtg tac      435
Arg Arg Phe Gln Lys Thr Trp Val Glu Lys Asn Pro Asp Tyr Val Tyr
            130                 135                 140 cac ctg att ccg gac tct gtg att gag gac ttt gtg gcg agt ttg tac      483
His Leu Ile Pro Asp Ser Val Ile Glu Asp Phe Val Ala Ser Leu Tyr
        145                 150                 155 gcg aac gtg ccg gag gtg gtc aga gcg tac cag ctg ctt ccg aaa aat      531
Ala Asn Val Pro Glu Val Val Arg Ala Tyr Gln Leu Leu Pro Lys Asn
    160                 165                 170 atc atg aag gcg gat ttt ttc cgg tat ttg gtg atc tac gcg cgc gga      579
Ile Met Lys Ala Asp Phe Phe Arg Tyr Leu Val Ile Tyr Ala Arg Gly
175                 180                 185                 190 ggc acc tac tca gac atg gac acg gtg tgt tta aag ccg atc aag gac      627
Gly Thr Tyr Ser Asp Met Asp Thr Val Cys Leu Lys Pro Ile Lys Asp
                195                 200                 205 tgg gcc acg ttt gat cgc gac ctg atc cac gct gcc gac aat aag gcc      675
Trp Ala Thr Phe Asp Arg Asp Leu Ile His Ala Ala Asp Asn Lys Ala
            210                 215                 220 gat ctc tcc cag ata gat cca gaa gca aga acc acg cct gtg ggg ctg      723
Asp Leu Ser Gln Ile Asp Pro Glu Ala Arg Thr Thr Pro Val Gly Leu
        225                 230                 235 gtg att ggc att gag gcc gac ccg gac agg ccc gac tgg cac gag tgg      771
Val Ile Gly Ile Glu Ala Asp Pro Asp Arg Pro Asp Trp His Glu Trp
    240                 245                 250
```

| | | |
|---|---|---|
| ttc tcg cgc aga ctg cag ttc tgc cag tgg acg atc cag gcg aag ccg<br>Phe Ser Arg Arg Leu Gln Phe Cys Gln Trp Thr Ile Gln Ala Lys Pro<br>255                      260                            265                           270 | | 819 |
| gga cac ccg ctg ctg cgc gag ctg atc atc cgg atc gtg gag gag acg<br>Gly His Pro Leu Leu Arg Glu Leu Ile Ile Arg Ile Val Glu Glu Thr<br>                  275                            280                            285 | | 867 |
| ttc cgc aaa cag cac atg ggc gtt ttg aaa aga gtg gaa ggc aag gac<br>Phe Arg Lys Gln His Met Gly Val Leu Lys Arg Val Glu Gly Lys Asp<br>                  290                            295                            300 | | 915 |
| tcg ggc gca gat atc atg cag tgg aca gga ccg ggg ata ttt aca gac<br>Ser Gly Ala Asp Ile Met Gln Trp Thr Gly Pro Gly Ile Phe Thr Asp<br>            305                            310                            315 | | 963 |
| act ctg ttt gat tat ctg aac aat gtg gcg agc gac ggc aag ttg ggc<br>Thr Leu Phe Asp Tyr Leu Asn Asn Val Ala Ser Asp Gly Lys Leu Gly<br>320                      325                            330 | | 1011 |
| gac ggg tac ggc gtg ggg tcg ttg tat tgg cgc aag cac ggc aaa tat<br>Asp Gly Tyr Gly Val Gly Ser Leu Tyr Trp Arg Lys His Gly Lys Tyr<br>335                      340                            345                            350 | | 1059 |
| aag ctg aaa aag aca gaa att aac aag aat aac gag cca ttg cat tct<br>Lys Leu Lys Lys Thr Glu Ile Asn Lys Asn Asn Glu Pro Leu His Ser<br>                  355                            360                            365 | | 1107 |
| gag gac cag ctt atc aac tgg agg tcg ctg acc aac atg gac aag cca<br>Glu Asp Gln Leu Ile Asn Trp Arg Ser Leu Thr Asn Met Asp Lys Pro<br>            370                            375                            380 | | 1155 |
| aag atc atg ggg gac gta atg gtg tta cca atc acg agc ttt agt ccg<br>Lys Ile Met Gly Asp Val Met Val Leu Pro Ile Thr Ser Phe Ser Pro<br>                  385                            390                            395 | | 1203 |
| aac gtg ggg cac atg ggc tca aag agc agc tca gat agg ctg gca ttt<br>Asn Val Gly His Met Gly Ser Lys Ser Ser Ser Asp Arg Leu Ala Phe<br>400                      405                            410 | | 1251 |
| gtg gag cat tta ttt tct ggc agc tgg aag cca aaa aac aaa<br>Val Glu His Leu Phe Ser Gly Ser Trp Lys Pro Lys Asn Lys<br>415                    420                            425 | | 1293 |
| taggaaaaat aaataattag ctgcatttta gataattctc atgagcaggc acagaacg | | 1351 |

<210> SEQ ID NO 2
<211> LENGTH: 428
<212> TYPE: PRT
<213> ORGANISM: Hansenula polymorpha

<400> SEQUENCE: 2

Met Val Tyr Phe Leu Asn Phe Met Ser Ile Thr Asn Val Pro Val Leu
1                  5                      10                    15

Lys Arg Ala Arg Leu Tyr Met Ala Thr Asn Arg Arg Leu Val Val Val
                20                      25                      30

Leu Val Val Leu Leu Tyr Trp Val Val Gln Asn Val Trp Thr Trp Ser
          35                      40                      45

Pro Gly Thr Arg Asp Leu Ala Gln Val Asp Ala Lys Ile Glu Ala Glu
    50                      55                      60

Leu Asn Ser Asn Leu His Thr Phe Gly Ala His Leu Arg His Leu Asn
65                    70                      75                    80

Arg Leu Pro Ala Glu Ser Ala Thr Leu Arg Glu Lys Leu Thr Phe Tyr
                85                      90                      95

Phe Pro Tyr Tyr Pro Glu Lys Pro Val Pro Asn Gln Ile Trp Gln Thr
            100                      105                    110

Trp Lys Val Asp Leu Glu Asp Asp Asn Phe Pro Lys Gln Tyr Arg Arg
                115                      120                    125

```
Phe Gln Lys Thr Trp Val Glu Lys Asn Pro Asp Tyr Val Tyr His Leu
    130                 135                 140
Ile Pro Asp Ser Val Ile Glu Asp Phe Val Ala Ser Leu Tyr Ala Asn
145                 150                 155                 160
Val Pro Glu Val Val Arg Ala Tyr Gln Leu Leu Pro Lys Asn Ile Met
                165                 170                 175
Lys Ala Asp Phe Phe Arg Tyr Leu Val Ile Tyr Ala Arg Gly Gly Thr
                180                 185                 190
Tyr Ser Asp Met Asp Thr Val Cys Leu Lys Pro Ile Lys Asp Trp Ala
            195                 200                 205
Thr Phe Asp Arg Asp Leu Ile His Ala Ala Asp Asn Lys Ala Asp Leu
    210                 215                 220
Ser Gln Ile Asp Pro Glu Ala Arg Thr Thr Pro Val Gly Leu Val Ile
225                 230                 235                 240
Gly Ile Glu Ala Asp Pro Asp Arg Pro Asp Trp His Glu Trp Phe Ser
                245                 250                 255
Arg Arg Leu Gln Phe Cys Gln Trp Thr Ile Gln Ala Lys Pro Gly His
                260                 265                 270
Pro Leu Leu Arg Glu Leu Ile Ile Arg Ile Val Glu Thr Phe Arg
            275                 280                 285
Lys Gln His Met Gly Val Leu Lys Arg Val Glu Gly Lys Asp Ser Gly
    290                 295                 300
Ala Asp Ile Met Gln Trp Thr Gly Pro Gly Ile Phe Thr Asp Thr Leu
305                 310                 315                 320
Phe Asp Tyr Leu Asn Asn Val Ala Ser Asp Gly Lys Leu Gly Asp Gly
                325                 330                 335
Tyr Gly Val Gly Ser Leu Tyr Trp Arg Lys His Gly Lys Tyr Lys Leu
            340                 345                 350
Lys Lys Thr Glu Ile Asn Lys Asn Asn Glu Pro Leu His Ser Glu Asp
    355                 360                 365
Gln Leu Ile Asn Trp Arg Ser Leu Thr Asn Met Asp Lys Pro Lys Ile
    370                 375                 380
Met Gly Asp Val Met Val Leu Pro Ile Thr Ser Phe Ser Pro Asn Val
385                 390                 395                 400
Gly His Met Gly Ser Lys Ser Ser Ser Asp Arg Leu Ala Phe Val Glu
                405                 410                 415
His Leu Phe Ser Gly Ser Trp Lys Pro Lys Asn Lys
            420                 425
```

<210> SEQ ID NO 3
<211> LENGTH: 36
<212> TYPE: DNA
<213> ORGANISM: Artificial Sequence
<220> FEATURE:
<223> OTHER INFORMATION: Synthetic

<400> SEQUENCE: 3
aaggaaaaaa gcggccgccg gtgaagaatg gtgtat                         36

<210> SEQ ID NO 4
<211> LENGTH: 39
<212> TYPE: DNA
<213> ORGANISM: Artificial Sequence
<220> FEATURE:
<223> OTHER INFORMATION: Synthetic

<400> SEQUENCE: 4

-continued

| | |
|---|---|
| tttccttttt gcggccgccg ttctgtgcct gctcatgat | 39 |

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5

| | |
|---|---|
| ggatccccgg gtaccgagct a | 21 |

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6

| | |
|---|---|
| caccggtagc taatgatccc | 20 |

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7

| | |
|---|---|
| cgaacatcca agtgggccga | 20 |

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8

| | |
|---|---|
| ctggcgaaag ggggatgtgc b | 21 |

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9

| | |
|---|---|
| ggcggatatg gggcttcgcc | 20 |

<210> SEQ ID NO 10
<211> LENGTH: 41
<212> TYPE: DNA
<213> ORGANISM: Artificial Sequence
<220> FEATURE:
<223> OTHER INFORMATION: Synthetic

<400> SEQUENCE: 10

| | |
|---|---|
| agctcggtac ccggggatcc cgttccaggg ctccacgtcc c | 41 |

<210> SEQ ID NO 11
<211> LENGTH: 41
<212> TYPE: DNA
<213> ORGANISM: Artificial Sequence

```
<220> FEATURE:
<223> OTHER INFORMATION: Synthetic

<400> SEQUENCE: 11
gcacatcccc ctttcgccag ccgatcacga gcttcagtcc d                41

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
cgtcgtccgg gcccagttcg                                        20

<210> SEQ ID NO 13
<211> LENGTH: 33
<212> TYPE: DNA
<213> ORGANISM: Artificial Sequence
<220> FEATURE:
<223> OTHER INFORMATION: Synthetic

<400> SEQUENCE: 13
ggggaattca aaaaaatggt ggtcttcagc aaa                         33

<210> SEQ ID NO 14
<211> LENGTH: 69
<212> TYPE: DNA
<213> ORGANISM: Artificial Sequence
<220> FEATURE:
<223> OTHER INFORMATION: Synthetic

<400> SEQUENCE: 14
gggccatggt cacaattcat catgcgcata gtcaggaaca tcgtatgggt atgtactact    60
cacccgcac                                                    69

<210> SEQ ID NO 15
<211> LENGTH: 435
<212> TYPE: PRT
<213> ORGANISM: Hansenula polymorpha

<400> SEQUENCE: 15

Met Ser Lys Ala Ser Pro Tyr Arg Gly Ile Asn Ser Thr Ser Ser Thr
1               5                   10                  15

Ser Pro Lys Phe Lys Lys Leu Ser Ile Phe Val Gly Leu Leu Leu Gly
            20                  25                  30

Leu Ile Leu Phe Lys Phe Ser Thr Ser Trp Ser Ile Asn Thr Glu Asp
        35                  40                  45

Lys Ile Val Ser Glu Tyr Leu Asn Asn Phe Tyr Lys Leu Asn Pro Lys
    50                  55                  60

Phe Arg Gly Ala Asn Pro Tyr Asp Ala Ala Val Thr Ala Glu Arg Leu
65                  70                  75                  80

Ala Lys Phe Phe Pro Tyr Asp Asn Ser Ala Arg Arg Ile Glu Lys Ser
                85                  90                  95

Ile Trp Gln Met Trp Lys Val Pro Ser Thr Asp Pro Asp Phe Pro His
            100                 105                 110

Lys Glu Leu Val Asn Lys Trp Lys Asn Glu Asn Pro Thr Tyr Lys Tyr
        115                 120                 125

Asn Leu Leu Thr Asp Asp Glu Ile Leu Glu Ile Leu Arg Ile Arg Phe
    130                 135                 140
```

```
Lys Asp Thr Val Pro Glu Val Leu Glu Ala Phe Glu Met Leu Pro Asn
145                 150                 155                 160

Lys Ile Ile Arg Ser Asp Phe Ala Arg Tyr Leu Leu Ile Phe Leu Asn
            165                 170                 175

Gly Gly Val Tyr Ala Asp Ile Asp Thr Asp Leu Gln Lys Pro Val Asp
            180                 185                 190

Thr Trp Phe Asp Ser Asp Arg Asn Val Gly Phe Val Ala Val Glu
        195                 200                 205

Glu Asp Ile Asn Val Glu Asn Trp Glu His Tyr Met Thr Arg Arg Ile
        210                 215                 220

Gln Phe Glu Gln Trp Thr Phe Lys Ala Lys Ala Lys His Pro Ile Leu
225                 230                 235                 240

Arg Lys Leu Ile Ala Lys Ile Val Glu Thr Thr Phe Gln Ala Lys Lys
                245                 250                 255

Asn Asp Lys Leu Gln Ala Tyr Tyr Lys Asp Phe Lys Gly Val Asp Arg
            260                 265                 270

Cys Ala Ser Val Asp Ile Met Val Trp Thr Gly Pro Val Val Trp Thr
        275                 280                 285

Asp Thr Ile Tyr Ala His Leu Asn Ser Ile Pro Ser Pro Thr Ile Val
        290                 295                 300

Asp Ile Asp His Gln Arg Asp Ile Ala Gly Glu Leu Tyr Gly Pro Glu
305                 310                 315                 320

Thr Gly Glu Gly Asp Val Ile Ser Trp Arg Phe Phe Ala Gly Leu Arg
            325                 330                 335

Ala Pro Val Met Ile Asp Asp Val Val Ile Tyr Pro Arg Ala Ser Phe
            340                 345                 350

Arg Glu Asp Lys Glu Asn Asn Cys Gly Lys Tyr Cys Tyr Val His His
        355                 360                 365

His Phe Gly Gly Ser Trp Lys Asn Asn Gly Lys Gly Glu Ile Lys Pro
        370                 375                 380

Gly Met Glu Gly Tyr Glu Gly Glu Asp Pro Asn Glu Val Glu Glu Leu
385                 390                 395                 400

Arg Lys Asn Asp Val Ser Lys Arg Asp Val Ile Pro Gly Glu Ser Lys
            405                 410                 415

Asp Val Ala Pro Val Lys Lys Leu Ala Lys Arg Cys Ala Tyr Pro Tyr
            420                 425                 430

Thr Pro Tyr
        435

<210> SEQ ID NO 16
<211> LENGTH: 385
<212> TYPE: PRT
<213> ORGANISM: Candida albicans
<220> FEATURE:
<221> NAME/KEY: misc_feature
<222> LOCATION: (384)..(385)
<223> OTHER INFORMATION: Xaa can be any naturally occurring amino acid

<400> SEQUENCE: 16

Met Leu Gln Leu Arg Glu Pro Gln Met Val His Lys His Leu Lys Leu
1               5                   10                  15

Ala Val Leu Gly Ile Val Val Ile Phe Thr Thr Tyr Phe Ile Ile Ser
            20                  25                  30

Ser Leu Ser Ser Pro Thr Ser Thr His Lys Thr Glu Tyr Asn Ser Pro
        35                  40                  45
```

```
Lys Leu Gln Leu Ala Lys Glu Leu Glu Leu Asn Ser Asn Trp Lys Glu
 50                  55                  60

Leu Gly Leu Asn Phe Gln Pro Asn Lys Lys Tyr Ser Leu Pro Asp Glu
 65                  70                  75                  80

Ser Thr Leu Arg Gln Gln Leu Ser Tyr Gln Phe Pro Tyr Asp Glu Ser
                 85                  90                  95

Lys Pro Phe Pro Lys Asn Ile Trp Gln Thr Trp Lys Val Gly Ile Asp
             100                 105                 110

Glu Lys Ser Phe Pro Lys Arg Tyr Leu Lys Tyr Gln Gln Thr Trp Glu
         115                 120                 125

Asp Lys Asn Pro Asp Tyr Lys His Tyr Val Val Pro Asp Lys Gln Cys
130                 135                 140

Asp Leu Leu Ile Glu Gln Leu Tyr Ser Gln Val Pro Asp Val Ala Lys
145                 150                 155                 160

Ala Tyr Arg Ile Met Pro Lys Ser Ile Leu Lys Ala Asp Phe Phe Arg
                165                 170                 175

Tyr Leu Ile Leu Phe Ala Arg Gly Gly Val Tyr Thr Asp Ile Asp Thr
            180                 185                 190

Val Gly Leu Lys Pro Val Asp Glu Trp Ile Ser Asn Ser Glu Met Ile
        195                 200                 205

Leu Glu Lys Lys Asn Arg Ser Gly Leu Val Val Gly Ile Glu Ala Asp
210                 215                 220

Pro Asp Arg Pro Asp Trp Ala Asp Trp Tyr Ala Arg Arg Ile Gln Phe
225                 230                 235                 240

Cys Gln Trp Thr Ile Gln Ser Lys Arg Gly His Pro Met Leu Arg Glu
                245                 250                 255

Leu Ile Ala Lys Ile Thr Asp Ile Thr Leu Thr Arg His Lys Lys Gly
            260                 265                 270

Gln Leu Lys Lys Val Leu Gly Lys Asn Glu Gly Gly Asp Ile Met Asn
        275                 280                 285

Trp Thr Gly Pro Gly Ile Phe Thr Asp Thr Val Phe Glu Tyr Met Asn
290                 295                 300

Asn Ile Leu Gln Ser Pro Glu Val Phe Lys Asn Lys Lys Lys Trp Ala
305                 310                 315                 320

Thr Ile Ile Asp Trp Lys Leu Phe Thr Gly Met Glu Gln Pro Ile Ala
                325                 330                 335

Ile Asp Asp Val Leu Val Leu Pro Ile Thr Ser Phe Ser Pro Asp Val
            340                 345                 350

Asn Gln Met Gly Ala Lys Asp Ser His Asp Pro Met Ala Tyr Ala Lys
        355                 360                 365

His Met Phe Ser Gly Ser Trp Lys Asp Asp Gly Met Pro Glu Met Xaa
    370                 375                 380

Xaa
385

<210> SEQ ID NO 17
<211> LENGTH: 404
<212> TYPE: PRT
<213> ORGANISM: Pichia pastoris

<400> SEQUENCE: 17

Met Ala Lys Ala Asp Gly Ser Leu Leu Tyr Tyr Asn Pro His Asn Pro
1               5                   10                  15

Pro Arg Tyr Tyr Phe Tyr Met Ala Ile Phe Ala Val Ser Val Ile
            20                  25                  30
```

Cys Val Leu Tyr Gly Pro Ser Gln Gln Leu Ser Ser Pro Lys Ile Asp
         35                  40                  45

Tyr Asp Pro Leu Thr Leu Arg Ser Leu Asp Leu Lys Thr Leu Glu Ala
 50                  55                  60

Pro Ser Gln Leu Ser Pro Gly Thr Val Glu Asp Asn Leu Arg Arg Gln
 65                  70                  75                  80

Leu Glu Phe His Phe Pro Tyr Arg Ser Tyr Glu Pro Phe Pro Gln His
                 85                  90                  95

Ile Trp Gln Thr Trp Lys Val Ser Pro Ser Asp Ser Ser Phe Pro Lys
                 100                 105                 110

Asn Phe Lys Asp Leu Gly Glu Ser Trp Leu Gln Arg Ser Pro Asn Tyr
             115                 120                 125

Asp His Phe Val Ile Pro Asp Ala Ala Trp Glu Leu Ile His His
         130                 135                 140

Glu Tyr Glu Arg Val Pro Glu Val Leu Glu Ala Phe His Leu Leu Pro
145                 150                 155                 160

Glu Pro Ile Leu Lys Ala Asp Phe Phe Arg Tyr Leu Ile Leu Phe Ala
                 165                 170                 175

Arg Gly Gly Leu Tyr Ala Asp Met Asp Thr Met Leu Leu Lys Pro Ile
                 180                 185                 190

Glu Ser Trp Leu Thr Phe Asn Glu Thr Ile Gly Val Lys Asn Asn
                 195                 200                 205

Ala Gly Leu Val Ile Gly Ile Glu Ala Asp Pro Asp Arg Pro Asp Trp
         210                 215                 220

His Asp Trp Tyr Ala Arg Arg Ile Gln Phe Cys Gln Trp Ala Ile Gln
225                 230                 235                 240

Ser Lys Arg Gly His Pro Ala Leu Arg Glu Leu Ile Val Arg Val Val
                 245                 250                 255

Ser Thr Thr Leu Arg Lys Glu Lys Ser Gly Tyr Leu Asn Met Val Glu
                 260                 265                 270

Gly Lys Asp Arg Gly Ser Asp Val Met Asp Trp Thr Gly Pro Gly Ile
             275                 280                 285

Phe Thr Asp Thr Leu Phe Asp Tyr Met Thr Asn Val Asn Thr Thr Gly
 290                 295                 300

His Ser Gly Gln Gly Ile Gly Ala Gly Ser Ala Tyr Tyr Asn Ala Leu
305                 310                 315                 320

Ser Leu Glu Glu Arg Asp Ala Leu Ser Ala Arg Pro Asn Gly Glu Met
                 325                 330                 335

Leu Lys Glu Lys Val Pro Gly Lys Tyr Ala Gln Gln Val Val Leu Trp
             340                 345                 350

Glu Gln Phe Thr Asn Leu Arg Ser Pro Lys Leu Ile Asp Asp Ile Leu
         355                 360                 365

Ile Leu Pro Ile Thr Ser Phe Ser Pro Gly Ile Gly His Ser Gly Ala
             370                 375                 380

Gly Asp Leu Asn His His Leu Ala Tyr Ile Arg His Thr Phe Glu Gly
385                 390                 395                 400

Ser Trp Lys Asp

<210> SEQ ID NO 18
<211> LENGTH: 480
<212> TYPE: PRT
<213> ORGANISM: Saccharomyces cerevisiae

<400> SEQUENCE: 18

```
Met Ser Arg Lys Leu Ser His Leu Ile Ala Thr Arg Lys Ser Lys Thr
1               5                   10                  15

Ile Val Val Thr Val Leu Leu Ile Tyr Ser Leu Leu Thr Phe His Leu
            20                  25                  30

Ser Asn Lys Arg Leu Leu Ser Gln Phe Tyr Pro Ser Lys Asp Asp Phe
        35                  40                  45

Lys Gln Thr Leu Leu Pro Thr Thr Ser His Ser Gln Asp Ile Asn Leu
    50                  55                  60

Lys Lys Gln Ile Thr Val Asn Lys Lys Asn Gln Leu His Asn Leu
65                  70                  75                  80

Arg Asp Gln Leu Ser Phe Ala Phe Pro Tyr Asp Ser Gln Ala Pro Ile
                85                  90                  95

Pro Gln Arg Val Trp Gln Thr Trp Lys Val Gly Ala Asp Asp Lys Asn
                100                 105                 110

Phe Pro Ser Ser Phe Arg Thr Tyr Gln Lys Thr Trp Ser Gly Ser Tyr
            115                 120                 125

Ser Pro Asp Tyr Gln Tyr Ser Leu Ile Ser Asp Ser Ile Ile Pro
    130                 135                 140

Phe Leu Glu Asn Leu Tyr Ala Pro Val Pro Ile Val Ile Gln Ala Phe
145                 150                 155                 160

Lys Leu Met Pro Gly Asn Ile Leu Lys Ala Asp Phe Leu Arg Tyr Leu
                165                 170                 175

Leu Leu Phe Ala Arg Gly Gly Ile Tyr Ser Asp Met Asp Thr Met Leu
            180                 185                 190

Leu Lys Pro Ile Asp Ser Trp Pro Ser Gln Asn Lys Ser Trp Leu Asn
    195                 200                 205

Asn Ile Ile Asp Leu Asn Lys Pro Ile Pro Tyr Lys Asn Ser Lys Pro
210                 215                 220

Ser Leu Leu Ser Ser Asp Glu Ile Ser His Gln Pro Gly Leu Val Ile
225                 230                 235                 240

Gly Ile Glu Ala Asp Pro Asp Arg Asp Asp Trp Ser Glu Trp Tyr Ala
                245                 250                 255

Arg Arg Ile Gln Phe Cys Gln Trp Thr Ile Gln Ala Lys Pro Gly His
                260                 265                 270

Pro Ile Leu Arg Glu Leu Ile Leu Asn Ile Thr Ala Thr Thr Leu Ala
                275                 280                 285

Ser Val Gln Asn Pro Gly Val Pro Val Ser Glu Met Ile Asp Pro Arg
    290                 295                 300

Phe Glu Glu Asp Tyr Asn Val Asn Tyr Arg His Lys Arg Arg His Asp
305                 310                 315                 320

Glu Thr Tyr Lys His Ser Glu Leu Lys Asn Asn Lys Asn Val Asp Gly
                325                 330                 335

Ser Asp Ile Met Asn Trp Thr Gly Pro Gly Ile Phe Ser Asp Ile Ile
                340                 345                 350

Phe Glu Tyr Met Asn Asn Val Leu Arg Tyr Asn Ser Asp Ile Leu Leu
                355                 360                 365

Ile Asn Pro Asn Leu Asn Lys Asn Asp Glu Glu Gly Ser Glu Ser Ala
                370                 375                 380

Thr Thr Pro Ala Lys Asp Val Asp Asn Asp Thr Leu Ser Lys Ser Thr
385                 390                 395                 400

Arg Lys Phe Tyr Lys Lys Ile Ser Glu Ser Leu Gln Ser Ser Asn Ser
                405                 410                 415
```

```
Met Pro Trp Glu Phe Phe Ser Phe Leu Lys Glu Pro Val Ile Val Asp
            420                 425                 430

Asp Val Met Val Leu Pro Ile Thr Ser Phe Ser Pro Asp Val Gly Gln
        435                 440                 445

Met Gly Ala Gln Ser Ser Asp Asp Lys Met Ala Phe Val Lys His Met
    450                 455                 460

Phe Ser Gly Ser Trp Lys Glu Asp Ala Asp Lys Asn Ala Gly His Lys
465                 470                 475                 480

<210> SEQ ID NO 19
<211> LENGTH: 396
<212> TYPE: PRT
<213> ORGANISM: Schizosaccharomyces pombe

<400> SEQUENCE: 19

Met Leu Arg Leu Arg Leu Arg Ser Ile Val Ile Gly Ala Ala Ile Ala
1               5                   10                  15

Gly Ser Ile Leu Leu Phe Asn His Gly Ser Ile Glu Gly Met Glu
            20                  25                  30

Asp Leu Thr Glu Ile Ser Met Leu Glu Asp Tyr Thr Pro Glu Ala Ala
        35                  40                  45

Asn Lys Asp Tyr Val Gly Gln Gln Glu Glu Glu Leu Leu Tyr Asp
    50                  55                  60

Gln Pro Ser Tyr Ile Glu Glu Glu Asp Pro Asp Leu Glu Ala Tyr
65              70                  75                  80

Leu Ser Asp Leu Glu Arg Glu Glu Leu Glu His Ser Leu Glu Glu Leu
                85                  90                  95

Asp Glu Glu Asn Asn Tyr Lys Leu His Leu Arg Tyr Ser Phe Ser Gln
            100                 105                 110

Leu Gln Asp Phe Asp Glu Glu Asn Glu Ala Val His Met Ile Val Pro
        115                 120                 125

Lys Asp Thr Tyr Glu Phe Glu Val Pro Tyr His Ala Asp Ile Pro Lys
    130                 135                 140

Leu Ile Trp Gln Thr Ser Lys Asp Pro Phe Asp Arg Glu Val Met Lys
145                 150                 155                 160

Tyr Thr Arg Phe Trp Arg Ile Asn His Pro Ser Tyr Ser His Ala Val
                165                 170                 175

Leu Asp Asp Glu Gln Ser Lys Ala Leu Val Ile Ser Ser Phe Gly Asp
            180                 185                 190

Ser Ser Val Ser Lys Ile Ser Gln Ala Tyr Ala Met Met Pro Leu Pro
        195                 200                 205

Val Leu Lys Ala Asp Phe Phe Arg Tyr Leu Val Leu Leu Ala Lys Gly
    210                 215                 220

Gly Ile Tyr Ser Asp Ile Asp Thr Ala Pro Leu Lys His Ile Asn Asn
225                 230                 235                 240

Trp Ile Pro Arg Glu Tyr Arg Lys Arg Asn Ile Arg Leu Ile Val Gly
                245                 250                 255

Ile Glu Ala Asp Pro Asp Arg Pro Asp Trp Asn Asp Tyr Tyr Ala Arg
            260                 265                 270

Arg Val Gln Phe Cys Gln Trp Thr Ile Ala Ala Ala Pro Gly His Pro
        275                 280                 285

Ile Leu Trp Glu Leu Val Arg Arg Ile Thr Asp Glu Thr Trp Lys Leu
    290                 295                 300

His Asp Ser Lys Lys Leu Ser Lys Asn Gly Glu Ser Val Met Glu Trp
305                 310                 315                 320
```

-continued

```
Thr Gly Pro Gly Ile Trp Thr Asp Ala Ile Met Asp Tyr Leu Asn Trp
            325             330                 335

Gln Tyr Gly Pro Phe Ser Val Glu Asn Ile Thr Asn Leu Glu Glu Pro
            340             345                 350

Tyr Leu Val Gly Asp Val Leu Ile Leu Pro Ile Thr Ala Phe Ser Pro
            355             360                 365

Gly Val Gly His Met Gly Ser Lys Ser Pro Asn Asp Pro Met Ala Tyr
            370             375                 380

Val Gln His Phe Phe Ala Gly Ser Trp Lys Asp Asp
385                 390             395
```

HANSENULA POLYMORPHA GENE CODING FOR α 1,6-MANNOSYLTRANSFERASE AND PROCESS FOR THE PRODUCTION OF RECOMBINANT GLYCOPROTEINS WITH HANSENULA POLYMORPHA MUTANT STRAIN DEFICIENT IN THE SAME GENE

TECHNICAL FIELD

The present invention relates to a novel *Hansenula polymorpha* gene coding for α-1,6-mannosyltransferase initiating outer chain elongation, an *H. polymorpha* mutant strain having a deficiency in the gene, and a process for producing a recombinant glycoprotein using such a mutant strain.

BACKGROUND ART

Upon large-scale expression of therapeutic proteins, according to characteristics of host cells or target proteins, a target protein may vary in expression levels, water solubility, expression sites, modification, and the like. Thus, the most suitable expression system for a target protein must be selected to establish an effective production system.

Most therapeutic proteins are glycoprotiens where oligosaccharides are covalently bonded to asparagine residues as they pass through the endoplasmic reticulum (ER) and Golgi apparatus (Jenkins et al., Nat. Biotechnol., 14, 975-9, 1996). The structure and kind of sugar moieties greatly affect folding, biological activity and stability in serum of glycoprotiens. Thus, to date, for producing therapeutic recombinant glycoproteins having wild-type sugar moieties and therapeutic activity, the most commonly used approach is to use animal cell expression systems. However, there are drawbacks to animal cell culture systems, which include low yield, high cost due to expensive culture media, retroviral contamination, and a long period of time required for establishing stable cell lines. Thus, animal cell culture systems have limited applications in producing recombinant glycoproteins. In this regard, many attempts have been made to use, as an alternative to animal cell expression systems, yeast expression systems, which are eukaryotes and share the early steps of the N-linked glycosylation pathway of higher animal cells, to produce recombinant glycoproteins of medical importance.

Eukaryotes such as yeasts have advantages of rapidly producing high-yield proteins, utilizing sterilized and well-controlled production conditions, being easily genetically engineered, having no risk of infections by human or animal pathogens, and ensuring easy protein recovery. However, a complete type synthesized in yeasts has a different sugar moiety from that of target organisms such as mammalians, and thus may cause immune responses in animal cells. Also, this yeast-specific outer chain glycosylation of the high mannose type, also denoted hyperglycosylation, brings rise to heterogeneity of a recombinant protein product, which may make the protein purification complicated or difficult. Further, the specific activity of enzymes may be lowered due to the increased carbohydrate level (Bekkers et al., Biochem. Biophy. Acta. 1089, 345-351, 1991).

To solve the above problems, there is a need for glycotechnology which introduces into yeasts a glycosylation pathway of animal cells capable of producing glycoproteins having identical biological activity to those derived from mammalians.

When recombinant glycoproteins are expressed in traditional yeast, *Saccharomyces cerevisiae*, the addition of a series of 50 to 200 mannose residues to a core oligosaccharide, resulting in hypermannosylation, and the presence of α-1,3-linked terminal mannose recognizable as an antigen in the body were viewed as large constraints in employing the yeast as a host for glycoprotein production (Dean, Biochim. Biophys. Acta., 1426, 309-322, 1999; Ballou, Methods Enzymol., 185, 440-444, (1990)). By contrast, when recombinant glycoproteins are expressed in the methylotropic yeasts, *Hansenula polymorpha* and *Pichia pastoris*, they are expressed in a hypermannosylated form compared to natural forms, but the overall length of mannose outer chains is shorter than those expressed in *S. cerevisiae* (Kang et al., Yeast 14, 371-381, 1998; Kim et al., Glycobioloby, in press, 2004; Bretthauer and Castellino, Biotechnol. Appl. Biochem. 30, 193-200, 1999). In particular, since sugar chains synthesized in the methylotrophic yeasts, *H. polymorpha* and *P. pastoris*, do not contain the strongly immunogenic α-1,3-linked terminal mannose (Kim et al., Glycobioloby, in press, 2004; Montesino et al., Protein Expr. Purif. 14, 197-207, 1998), the methylotrophic yeasts are considered superior host systems to traditional yeast, *S. cerevisiae*, for the production of glycoproteins having therapeutic value in humans.

Many attempts were made in the glycotechnology field to develop hosts capable of producing therapeutic recombinant glycoproteins containing human compatible sugar chains using *P. pastoris* and *S. cerevisiae* (Chiba et al., J. Biol. Chem., 273, 26298-26304, 1998; Callewaert et al., FEBS Lett., 503, 173-178, 2001; Choi et al., Proc. Natl. Acad. Sci. USA, 100, 5022-5027, 2003; Hamilton et al., Science, 301, 1244-1246, 2003). For example, an attempt was made to produce a glycoprotein where an intermediate including the human mannose-type $Man_5GlcNAc_2$ N-glycan was attached using a recombinant *S. cerevisiae* obtained by further genetically manipulating a triple mutant yeast (och1Δmnn1Δmnn4Δ) to express mammalian α-1,2-mannosidase in the ER (Chiba et al., J. Biol. Chem., 273, 26298-26304, 1998). The triple mutant has disruption in three genes: OCH1 that plays a critical role in outer chain initiation (Nakanishi-Shindo et al., J. Biol. Chem. 268, 26338-26345, 1993; U.S. Pat. No. 5,705,616; U.S. Pat. No. 5,798,226); MNN1 that mediates addition of the immunogenic α-1,3-linked terminal mannose (Gopal and Ballou, Proc. Natl. Acad. Sci. USA 84, 8824, (1987); U.S. Pat. No. 5,135,854); and MNN4 that addes phosphates to a sugar chain (Jigami and Odani, Biochim. Biophys. Acta., 1426, 335-345, 1999). In addition, according to recent studies (Choi et al., Proc. Natl. Acad. Sci. USA, 100, 5022-5027, 2003; Hamilton et al., Science, 301, 1244-1246, 2003), host developments in *P. pastoris* were made to produce recombinant glycoproteins with the human complex-type N-glycan $GlcNAc_2Man_3GlcNAc_2$ by introducing five different enzymes derived from eukaryotes into a secretory pathway in order to introduce the human glycosylation pathway into mutant strains (Japanese Pat. 07145005; Japanese Pat. 07150780; International Pat. Publication WO 0200856 A2; International Pat. Publication WO 0200879 A2) which have a disruption in the OCH1 gene mediating outer chain initiation. However, to date, from the viewpoint of glycotechnlgy, attempts have rarely been made to produce recombinant glycoproteins with human-type sugar chains in the methylotropic yeast *H. polymorpha* which is gaining popularity as a host for the expression of therapeutic recombinant proteins since it has been employed for producing hepatitis vaccines.

As described in Korean Pat. Application No. 2002-37717, the present inventors, before the present invention, cloned OCH1 gene playing a critical role in the outer chain synthesis of *H. polymorpha*, establishing a mutant strain (Hpoch1Δ) having a disrupted OCH1 gene, and developed a process for producing a recombinant glycoprotein with a sugar chain structure closer to a natural form by preventing hyperglycosylation using such a mutant. However, in the Hpoch1Δ mutant strain having a disruption in the OCH1 gene of *H. polymorpha*, outer chain glycosylation is still initiated by α-1,6-mannose linkage. Thus, there is a need for the finding of a gene coding for α-1,6-mannosyltransferase and prevention of the above human incompatible glycosylation pathway.

DISCLOSURE OF THE INVENTION

With an aim to overcome the above problems and develop a production system for a recombinant glycoprotein having therapeutic value in humans using a methylotrophic, thermotolerant yeast *Hansenula polymorpha* that is widely used as a host system for mass expression of various heterogeneous genes, the present inventors cloned a novel gene HpOCH2 in a *H. polymorpha* strain DL-1 based on the known genome information for *H. polymorpha*, identified that the novel gene has the activity of α-1,6-mannosyltransferase responsible for the outer chain initiation, and developed a mutant strain having a disruption in the above gene. Then, the present inventors found that the mutant strain prevents a human incompatible glycosylation pathway, and, when a heterogeneous sugar chain-modifying enzyme is expressed in the mutant strain, is capable of producing a recombinant glycoprotein with a human mannose-type N-glycan $Man_5GlcNAc_2$ other than a yeast-specific N-glycan, thereby leading to the present invention.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows a nucleotide sequence of *H. polymorpha* HpOCH2 gene and its predicted amino acid sequence, wherein a transmembrane spanning region is underlined, and an amino acid sequence corresponding to a DXD element is bold and underlined;

FIG. 2 is a multiple alignment of amino acid sequences of Och1 protein analogues of *H. polymorpha* and other yeast strains (HpOch2p: *H. polymorpha* Och2 protein; HpOch1p: *H. polymorpha* Och1 protein; CaOch1p: *Candida albicans* Och1 protein; PpOch1p: *Pichia pastoris* Och1 protein; ScOch1p: *Saccharomyces cerevisiae* Och1 protein; and SpOch1p: *Schizosaccharomyces pombe* Och1 protein), wherein parenthesized numerals indicate amino acid identity between *H. polymorpha* HpOch2p and Och1p analogues of other yeast strains;

FIG. 3 is a diagram for inducing disruption of the *H. polymorpha* HpOCH2 gene by in vivo DNA recombination;

FIG. 6 shows results of tests for functional compensation of a *S. cerevisiae* och1Δ mutant by introduction of HpOCH2 gene (1: *S. cerevisiae* wild type transformed with a control vector YEp352GAPII; 2: *S. cerevisiae* och1Δ mutant (Scoch1Δ) transformed with the control vector; and 3, 4 and 5: Soch1Δ mutant transformed respectively with an HpOCH1 gene expression vector YEp352GAPII-HpOCH1 (3), an HpOCH2 gene expression vector YEp352GAPII-HpOCH2 (4), and a ScOCH1 gene expression vector YEp352GAPII-ScOCH1 (5)), wherein yeast cultures ($OD_{600}=1$) which had arrived at an exponential phase were 10-fold serially diluted, and 3 µl of each dilution was spotted on a YPD plate and cultured at 25° C. and 30° C. for three days (the A of FIG. 6); and gylcosylation of invertase expressed in each transformant was detected by activity staining (the B of FIG. 6);

FIG. 9 shows amino acid sequence identity and similarity between Och1 protein homologues of *S. cerevisiae* and *H. polymorpha*.

BEST MODE FOR CARRYING OUT THE INVENTION

Figure 4:
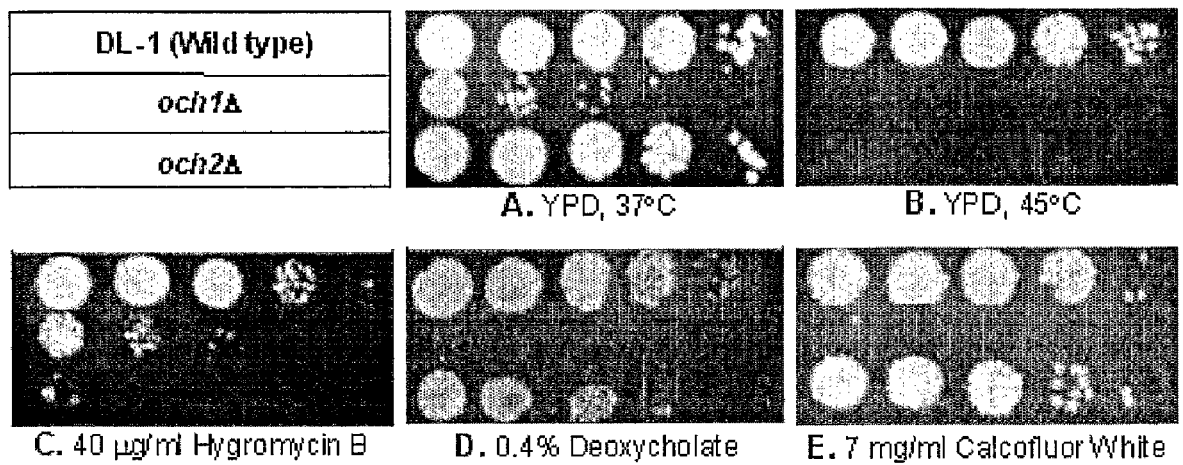
FIG. 4 shows growth properties of an *H. polymorpha* Hpoch2Δ mutant strain, wherein cultures ($OD_{600}=1$) of a *H. polymorpha* wild type and two mutant strains, Hpoch1Δ and Hpoch2Δ, which had arrived at an exponential phase, were 10-fold serially diluted, and 3 µl of each dilution was spotted on a YPD medium and cultured for two days (A: YPD medium at 37° C.; B:YPD medium at 45° C.; C:YPD medium supplemented with 40 µg/ml hygromycine B; D: YPD medium supplemented with 0.4% sodium deoxycholate; and E: YPD medium supplemented with 7 µg/ml Calcofluor white)

In eukaryotes, protein N-glycosylation originates in the endoplasmic reticulum (ER), where an N-linked oligosaccharide ($Glc_3Man_8GlcNAc_2$) is transferred to an appropriate asparagine residue of a nascent protein. From $Glc_3Man_8GlcNAc_2$, three glucose residues and one specific α-1,2-linked mannose residue are removed by specific glucosidases and α-1,2-mannosidase in the ER, resulting in the core oligosaccharide structure, $Man_8GlcNAc_2$. The protein with this core sugar structure is transported to the Golgi apparatus where the sugar moiety undergoes various modifications by various specific enzymes. In yeasts, the modification of the sugar chain in the Golgi apparatus involves a series of additions of mannose residues by different mannosyltransferases. The structure of the outer chain glycosylation is specific to the organisms, typically with more than 50 mannose residues in *S. cerevisiae*.

The present inventors cloned an HpOCH2 gene in a *H. polymorpha* strain DL-1 based on the known genome information for *H. polymorpha*, and identified that the above gene has the activity of α-1,6-mannosyltransferase responsible for the outer chain initiation. The identified gene has a nucleotide sequence designated as SEQ ID NO. 1, and its corresponding amino acid sequence is designated as SEQ ID NO. 2.

In one aspect, the present invention provides a DNA gene coding for a protein designated as SEQ ID NO. 2. In addition, the present invention provides a DNA gene coding for a protein having a 75% or higher homology with the former DNA and coding for a protein with α-1,6-mannosyltransferase enzyme activity. Preferably, the present invention provides a gene having a DNA sequence designated as SEQ ID NO. 1, an analogue thereof or a fragment thereof.

The term "homology", as used for a α-1,6-mannosyltransferase gene derived from *H. polymorpha* in the present invention, is intended to indicate the degree of similarity to the nucleotide sequence of a wild type, and includes a DNA sequence having an identity of preferably 75% or higher, more preferably 85% or higher, and most preferably 90% or higher, with a DNA sequence coding for α-1,6-mannosyltransferase. This homology comparison may be performed manually or by using a commercially available comparison program. A commercially available computer program may express homology between two or more sequences as a percentage, and a homology (%) may be calculated for adjacent sequences.

The present inventors registered the above gene at GenBank under accession number AY502025, and deposited a recombinant vector containing the gene, pBS-HpOCH2/*Escherichia coli* DH5@, at KCTC (Korean Collection for Type Cultures; KRIBB, 52, Oun-dong, Yusong-ku, Taejon, Korea) on Jan. 15, 2004, under accession number KCTC 10583BP.

Thus, in another aspect, the present invention provides a recombinant vector comprising a gene which is DNA coding for a protein designated as SEQ ID NO. 2 or DNA having a 90% or higher homology with the former DNA and coding for a protein with α-1,6-mannosyltransferase activity. The recombinant vector preferably comprises a DNA gene designated as SEQ ID NO. 1. In a further aspect, the present invention provides a host cell transformed with the recombinant vector, and preferably, provides a transformed host cell deposited under accession number KCTC 10583BP.

To produce a glycoprotien having a mammalian-type sugar chain in a yeast, a mutant strain yeast should be established, which lacks an enzyme family involved in yeast outer chain biosynthesis. Such a mutant strain may be attained by genetic mutation such as use of a reagent, ultraviolet illumination or spontaneous mutation, or by artificially disrupting a target gene. In the present invention, a gene (Och2) encoding α-1,6-mannosyltransferase playing a critical role in the outer chain initiation is disrupted by genetic engineering methods, that is, a combination of polymerase chain reaction and in vivo DNA recombination.

The present inventors established a *Hansenula polymorpha* Hpoch2Δ mutant strain (*Hansenula polymorpha* DL-1 och2Δ) in which a α-1,6-mannosyltransferase gene identified as described above is deficient, and found that yeast-specific consecutive addition of α-1,6-mannose residues is prevented in the mutant strain, so that hyperglycosylation is remarkably reduced. The mutant strain was deposited at KCTC (Korean Collection for Type Cultures; KRIBB, 52, Oun-dong, Yusong-ku, Taejon, Korea) on Jan. 15, 2004, under accession number KCTC 10584BP.

Thus, in yet another aspect, the present invention provides a *Hansenula polymorpha* Hpoch2Δ mutant strain (*Hansenula polymorpha* DL-1 och2Δ) deposited under accession number KCTC 10584BP.

The majority of N-glycans on glycoproteins transported from the ER have a $Man_8GlcNAc_2$ sugar chain structure. After a protein is transported to the Golgi apparatus from the ER, additional mannose residues are added to the protein by different mannosyltransferases, resulting in a glycoprotien having numerous mannose sugar chains. The hyperglycosylation is undesirable in recombinant glycoproteins. Such hyperglycosylation may be reduced by using the *H. polymorpha* mutant strain prepared in the present invention as a host cell for the expression of recombinant proteins. In addition, when the *H. polymorpha* mutant strain is transformed with an expression vector capable of expressing one or more proteins having an enzymatic activity involved in sugar chain modifications, the hyperglycosylation may be more effectively inhibited or be converted to a sugar chain with a different structure. Sugar chain-modifying enzymes involved in such hyperglycosylation reduction include α-1,2-mannosidase, mannosidase IA, mannosidase IB, mannosidase IC, mannosidase II, N-acetyl glucosaminyltransferase I, N-acetyl glucosaminyltransferase II, galactosyltransferase, sialyltransferase, and fucosyltransferase. However, the present invention is not limited to the above examples, and various genes capable of leading to a reduction and modification in hyperglycosylation of a recombinant glycoprotein may be also used. In an embodiment of the present invention, when α-1,2-mannosidase was expressed in the *H. polymorpha* Hpoch2Δ mutant strain, a recombinant glycoprotein on which a yeast-type N-glycan was prevented from being formed and modified to a human-type N-glycan was produced. α-1,2-mannosidase removes a α-1,2-linked mannose residue at a non-reduced terminal of $Man_8GlcNAc_2$ and converts a core sugar chain on this glycoprotein to $Man_5GlcNAc_2$. The $Man_5GlcNAc_2$ structure is an inferior substrate for Golgi-residing mannosyltransferases, leading to a glycoprotein having reduced mannose content. The sugar chain-modifying enzyme gene contained in the expression vector used in the transformation may be the whole gene sequence encoding such an enzyme or a fragment sequence encoding a functional region of the enzyme. The expression vector includes an integrative or inductive promoter and a 3' termination sequence, and may be an integrative or replicative vector.

Thus, in still another aspect, the present invention provides a *H. polymorpha* mutant strain further comprising an expression vector expressing a sugar chain-modifying enzyme. Preferably, the sugar chain-modifying enzyme is selected from the group consisting of α-1,2-mannosidase, mannosidase IA, mannosidase IB, mannosidase IC, mannosidase II, N-acetyl glucosaminyltransferase I, N-acetyl glucosaminyltransferase II, galactosyltransferase, sialyltransferase, and fucosyltransferase.

In still another aspect, the present invention provides a process for producing a recombinant glycoprotein with reduced glycosylation using an *H. polymorpha* mutant strain deposited under accession number KCTC 10584BP.

According to the present process as described above, a recombinant glycoprotein may be produced in a manner such that formation of a yeast-type N-glycan is prevented and the yeast-type N-glycan is modified to a human-type N-glycan.

The term "glycoprotein", as used herein, refers to a protein that is glycosylated on one or more asparagines, or one or more serine or threonine residues, or is glycosylated on asparagine and serine or threonine residues when expressed in a methylotropic yeast, particularly *Hansenula polymorpha*. The term "reduced glycosylation", as used herein, means that, when a glycoprotein is expressed in a methylotropic yeast strain, it has a reduced size of a carbohydrate moiety, particularly lower mannose residues, in comparison with the case of being expressed in a wild-type methylotropic yeast.

In the above process, a glycoprotein expression vector introduced into the *Hansenula polymorpha* Hpcho2Δ mutant strain preferably expresses a sugar chain-modifying enzyme such as α-1,2-mannosidase along with glycoprotein.

A produced glycoprotein may be purified by a method commonly used in the art, and a purification protocol may be determined according to the properties of a specific protein to be purified. This determination is considered an ordinary skill to those skilled in the art. For example, a target protein may be purified by a typical isolation technique, such as precipitation, immoadsorption, fractionization or various chromatographic methods.

Glycoproteins capable of being produced according to the present invention are exemplified by cytokines (e.g., interferon-α, interferon-β, interferon-γ, G-CSF, etc.), clotting factors (e.g., VIII factor, IX factor, human protein C), endothelial growth factor, growth hormone releasing factor, *Penicillium minioluteum* dextranase, *Bacillus amyloliquefaciens* α-amylase, *Saccharomyces cerevisiae* aspartic protease, *Saccharomyces cerevisiae* invertase, *Typanosoma cruzi* trans-sialidase, HIV envelope protein, influenza virus A haemagglutinin, influenza neuraminidase, bovine enterokinase activator, bovine herpes virus type-1 glycoprotein D, human angiostatin, human B7-1, B7-2 and B-7 receptor CTLA-4, human tissue factor, growth factors (e.g., platelet-derived growth factor), human α-antitrypsin, human erythropoietin, tissue plasminogen activator, plasminogen activator inhibitor-1, urokinase, α-galactosidase, plasminogen, thrombin, and immunoglobulins.

In still another aspect, the present invention provides a glycoprotein produced by the above process.

A better understanding of the present invention may be obtained through the following examples which are set forth to illustrate, but are not to be construed as the limit of the present invention.

Example 1

Identification of *Hansenula polymorpha* HpOCH2 Gene and Analysis of the Amino Acid Sequence of the Gene From the recently completed sequence of *Hansenula polymorpha* RB11 genome (Ramezani-Rad et al., FEMS Yeast Res., 4, 207-215 (2003)), whole sequences of ORFs (open reading frames) having a high similarity with the OCH1 gene family involved in outer chain biosynthesis of *Saccharomyces cerevisiae* were obtained. FIG. 9 shows amino acid sequence identity and similarity between Och1 protein homologues of *H. polymorpha* and *S. cerevisiae*, wherein the amino acid sequence identity and similarity between ORF168 and ScOch1p are represented by shaded bold numerals.

In the present invention, for functional analysis of the ORF168 gene having a 40% amino acid identity and a 54% amino acid similarity with *S. cerevisiae* OCH1 gene (ScOCH1) (Jungman and Munro, Embo J. 17, 423 (1998)) that plays a critical role in α-1,6-mannose addition at the early stage of outer chain biosynthesis of *S. cerevisiae*, polymerase chain reaction (PCR) was carried out using DNA extracted from *Hansenula polymorpha* DL-1 (Levine and Cooney, Appl. Microbiol., 26, 982-990, (1973)) as a template and a pair of primers (168Not-N and 168Not-C; Table 1). As a result, a 1.35-kb DNA fragment containing the ORF168 was obtained, and was then subjected to amino acid sequencing.

A conventionally identified *H. polymorpha* gene described in Korean Pat. Application No. 2002-37717 applied by the present inventors has an amino acid sequence having a 22% identity and a 36% similarity with *S. cerevisiae* OCH1 gene and is thus designated as HpOCH1. In this regard, the ORF168 identified in this invention was designated as HpOCH2, and its nucleotide sequence was registered at GenBank under accession number AY502025. HpOCH2 was 1287 bp long and expected to code for a protein consisting of 428 amino acids. HpOch2 protein had a potential transmembrane spanning region at a region from 29 to 51 positions, and was thus considered as a type II membrane protein to which most glycosyltransferases belong (FIG. 1). Also, HpOch2 protein was observed to have a DXD element known as an active site of glycosyltransferases (Lussier et al., J. Cell. Biol., 131, 913-927, (1995)), and was thus expected to have glycosyltransferase activity (FIG. 1). The amino acid sequence of HpOch2 protein was found to have a relatively high similarity with, in addition to a *S. cerevisiae* OCH1 gene product, OCH1 gene products of other yeasts, that is, *Candida albicans*: Thomas et al., unpublished results, GenBank accession number AY064420), *Pichia pastoris*: Japanese Pat. 07145005), *Schizosaccharomyces pombe*: Yoko-o et al., FEBS Lett., 489, 75-80, (2001)) (FIG. 2).

Example 2

Establishment of *H. polymorpha* HpOCH2 Gene-Deficient Strain and Analysis of Characteristics of the Strain To establish a *H. polymorpha* HpOCH2 gene-deficient mutant strain, gene disruption was performed by a combination of fusion PCR and in vivo DNA recombination (Oldenburg et al., Nucleic Acid Res., 25, 451, (1997)). Fusion PCR was carried out using primers (primers used for PCR for cloning and disruption of HpOCH2 gene) listed in Table 1, below. By primary PCR, 5' and 3' regions of URA3 gene and HpOCH2 gene were obtained. By secondary fusion PCR, the 5' region of HpOCH2 gene was linked to the 5' region of URA3 gene, and the 3' region of URA3 gene was liked to the 3' region of HpOCH2 gene. Then, the two DNA fragments were introduced into a yeast cell, and transformants having an HpOCH2 gene disrupted by in vivo DNA recombination were selected (FIG. 3). Primarily, using an URA3 selection marker, transformants grown in a minimum medium lacking uracil were selected. Then, amplified DNA fragments produced by PCR were examined to determine whether they differ from those of a wild-type strain, thereby selecting a *H. polymorpha* mutant strain having a different amplification pattern, Hpoch2Δ (leu2 och1::URA3). The obtained Hpoch2Δ strain was evaluated for growth properties. The Hpoch2Δ strain was found to have temperature sensitivity at 45° C. like a Hpoch1Δ strain (KCTC 10264BP), but, unlike the Hpoch1Δ strain, had a similar growth rate to the wild type at 37° C. Also, growth was greatly inhibited in the presence of hygromycin B, and little sensitivity to sodium deoxycholate was observed (FIG. 4). Since these growth properties are common in mutant strains having a defect in outer chain synthesis, the *H. polymorpha* Hpoch2Δ strain was believed to have a defect in the outer chain glycosylation process.

TABLE 1

| Primer | Sequences | SEQ ID. No. |
|---|---|---|
| 168Not-N | 5'-AAGGAAAAAAGCGGCCGCCGGTGAAGAATGGTGTAT-3' | 3 |
| 168Not-C | 5'-TTTTCCTTTTGCGGCCGCCGTTCTGTGCCTGCTCATGAT-3' | 4 |
| UNfor | 5'-GGATCCCCGGGTACCGAGCT-3'[a] | 5 |
| UNrew | 5'-CACCGGTAGCTAATGATCCC-3' | 6 |
| UCfor | 5'-CGAACATCCAAGTGGGCCGA-3' | 7 |
| UCrew | 5'-CTGGCGAAAGGGGGATGTGC-3'[b] | 8 |
| 168Nfor | 5'-GGCGGATATGGGGCTTCGCC-3' | 9 |
| 168Nrew | 5'-AGCTCGGTACCCGGGGATCCCGTTCCAGGGCTCCACGTCC-3'[c] | 10 |
| 168Cfor | 5'-GCACATCCCCCTTTCGCCAGCCGATCACGAGCTTCAGTCC-3'[d] | 11 |
| 168Crew | 5'-CGTCGTCCGGGCCCAGTTCG-3' | 12 |

Example 3

Figure 5:
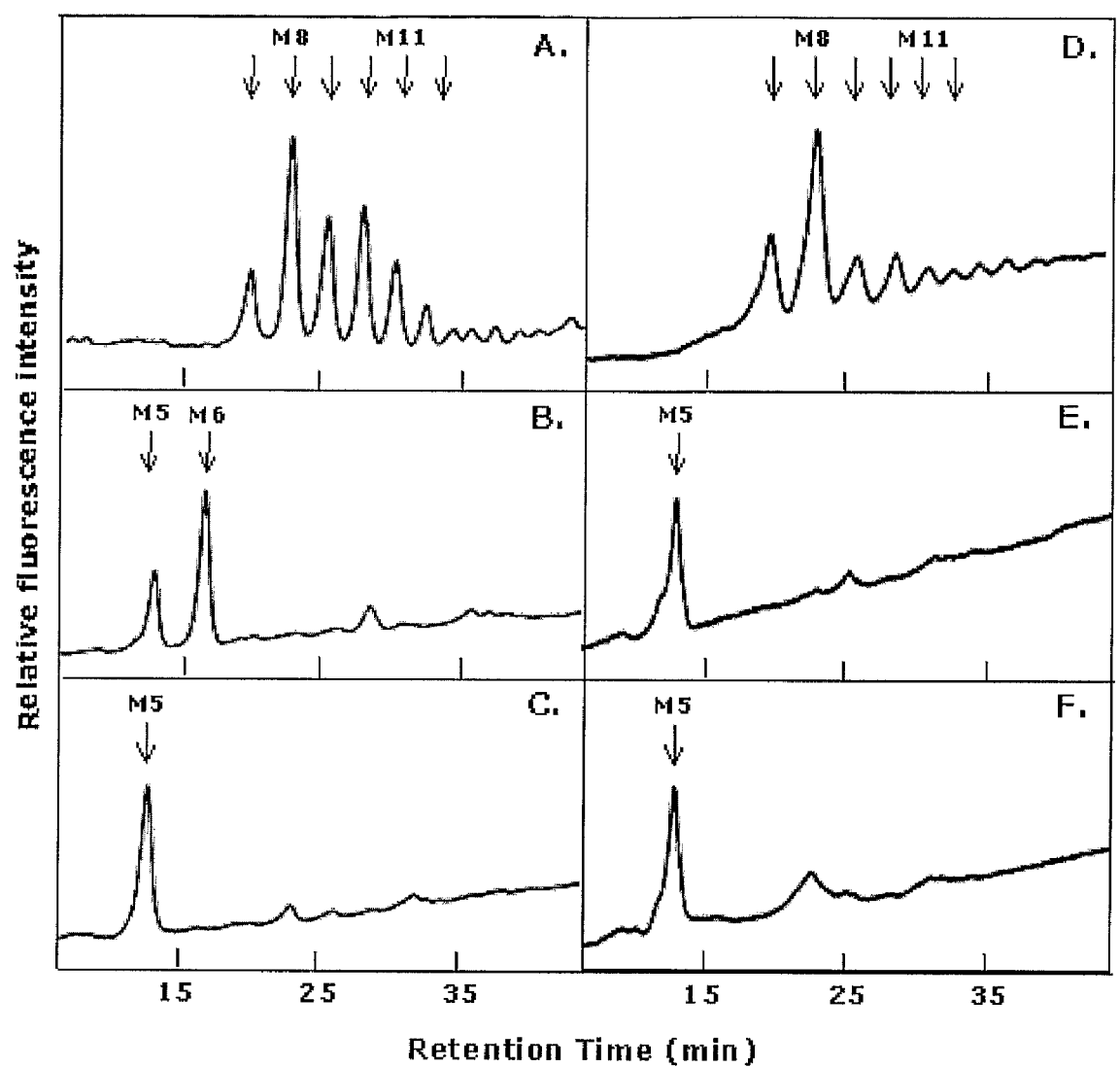
FIG. 5 shows results of HPLC analysis for size distribution and structure of sugar chains attached to glucose oxidase (GOD) expressed in an *H. polymorpha* Hpoch2Δ mutant strain, wherein the left panel (A, B and C) and right panel (D, E and F) represent results for sugar chains attached to GOD expressed respectively in an *H. polymorpha* wild type and the Hpoch2Δ mutant (A and D: sugar chain profiles attached to GOD; B and E: sugar chain profiles after treatment with α-1,2-mannosidase; and C and F: sugar chain profiles after subsequent treatment with α-1,6-mannosidase), and retention times of standard oligosaccharides of known size and structure are indicated by arrows (M5: $Man_5GlcNAc_2$-PA; M6: $Man_6GlcNAc_2$-PA; M8: $Man_8GlcNAc_2$-PA; and M11: $Man_{11}GlcNAc_2$-PA)

Analysis of Size Distribution and Structure of Sugar Chains on a Glycoprotein Synthesized in the *H. polymorpha* Hpoch2Δ Mutant To analyze the size distribution and structure of sugar chains on glycoprotein synthesized in the *H. polymorpha* Hpoch2Δ mutant prepared in Example 2, a glycoprotein derived from *Aspergillus niger*, glucose oxidase (GOD), was expressed in a secreted form in a *H. polymorpha* wild type and the Hpoch2Δ mutant. The glycoprotein, GOD, has eight putative amino acid sequences for N-linked glycosylation (Frederick et al., J. Biol. Chem., 265, 3793 (1990)). The *H. polymorpha* wild type and Hpoch2Δ mutant were individually transformed with an expression vector pDLMOX-GOD(H) expressing GOD with a six-histidine tag (Kim et al., Glycobiology (2004)), and were grown in YPM medium (1% yeast extract, 2% peptone, 2% methanol) supplemented with 2% methanol to express GOD. GOD secreted to the culture medium was passed through a nickel column to selectively isolate only GOD tagged with six histidines at the C-terminal region. The isolated recombinant his-tagged GOD was treated with PNGase F to detach attached sugar chains from the GOD. Then, the released sugar chains were labelled with 2-aminopyridine (2-PA) and subjected to HPLC analysis. As shown in the A and D of FIG. 5, sugar chains of wild type-derived recombinant GOD were found to have various size distributions ranging from 8 to 12 mannose residues. In contrast, sugar chains attached to recombinant GOD expressed in the Hpoch2Δ mutant were found to mostly have core sugar chains with 8 mannose residues. These results indicate that sugar addition after the eighth mannose residue is greatly inhibited in the Hpoch2Δ mutant. Separately, the sugar chains released from recombinant GOD were treated sequentially by α-1,2-mannosidase and α-1,6-mannosidase to investigate changes in a sugar chain profile. Sugar chains synthesized by the wild type were converted to sugar chains corresponding to five or six mannose, and all of them were then converted to sugar chains corresponding to five mannose by α-1,6-mannosidase, whereas all sugar chains of the Hpoch2Δ mutant were converted to sugar chains corresponding to five mannose by only α-1,2-mannosidase (FIG. 5). These results reveal that initiation of outer chain elongation via α-1,6-mannose linkage never occurs in the Hpoch2Δ mutant, thereby indicating that the HpOCH2 gene product is directly or indirectly involved in the activity of α-1,6-mannosidase.

Example 4

Functional Analysis of *H. polymorpha* HpOCH2 Protein

To determine whether the *H. polymorpha* HpOCH2 gene product is a functional homologue to *S. cerevisiae* Och1 protein adding α-1,6 mannose to a core sugar chain in the outer chain synthesis initiation process, an expression vector carrying an HpOCH2 gene, YEp352GAPII-HpOCH2, was introduced into a mutant strain having a disruption in *S. cerevisiae* OCH1 gene, Scoch1Δ, and the Scoch1Δ mutant was evaluated for ability to overcome thermosensitivity (the A of FIG. 6). HpOCH2, HpOCH1 and ScOCH1 genes were individually inserted between glyceraldehyde-3-phosphate dehydrogenase (GAP) promoter and terminator introduced into a *S. cerevisiae* expression vector YEp352 (Hill et al., Yeast, 2, 163-167, (1986)), thus generating expression vectors, YEp352GAPII-HpOCH2, YEp352GAPII-HpOCH1 and YEp352GAPII-ScOCH1, respectively. The *S. cerevisiae* Scoch1Δ mutant, when transformed with the HpOCH2 gene expression vector (YEp352GAPII-HpOCH2), recovered its ability to grow at high temperature. By contrast, when transformed with the expression vector (YEp352GAPII-HpOCH1) carrying HpOCH1 gene having a nucleotide sequence similarity to HpOCH2 gene, the Scoch1Δ mutant did not overcome thermosensitivity (the A of FIG. 6). In addition, the Scoch1Δ mutant was evaluated for another feature of having a defect in hyperglycosylation. When the HpOCH2 expression vector was introduced into the Scoch1Δ mutant, as shown in the B of FIG. 6, the glycosylation of a glycoprotein, invertase, recovered to a level identical to that when the OCH1 expression vector (YEp352GAPII-ScOCH1) was introduced thereinto. By contrast, when the HpOCH2 expression vector was introduced into the Scoch1Δ mutant, glycosylation of invertase was unchanged. The results, that the *S. cerevisiae* och1Δ mutant overcomes thermosensitivity and recovers hyperglycosylation by the expression of *H. polymorpha* HpOCH2 gene, demonstrate that the HpOCH2 gene product is a functional analogue to *S. cerevisiae* Och1 protein playing a critical role in the first step of outer chain synthesis.

Figure 7:
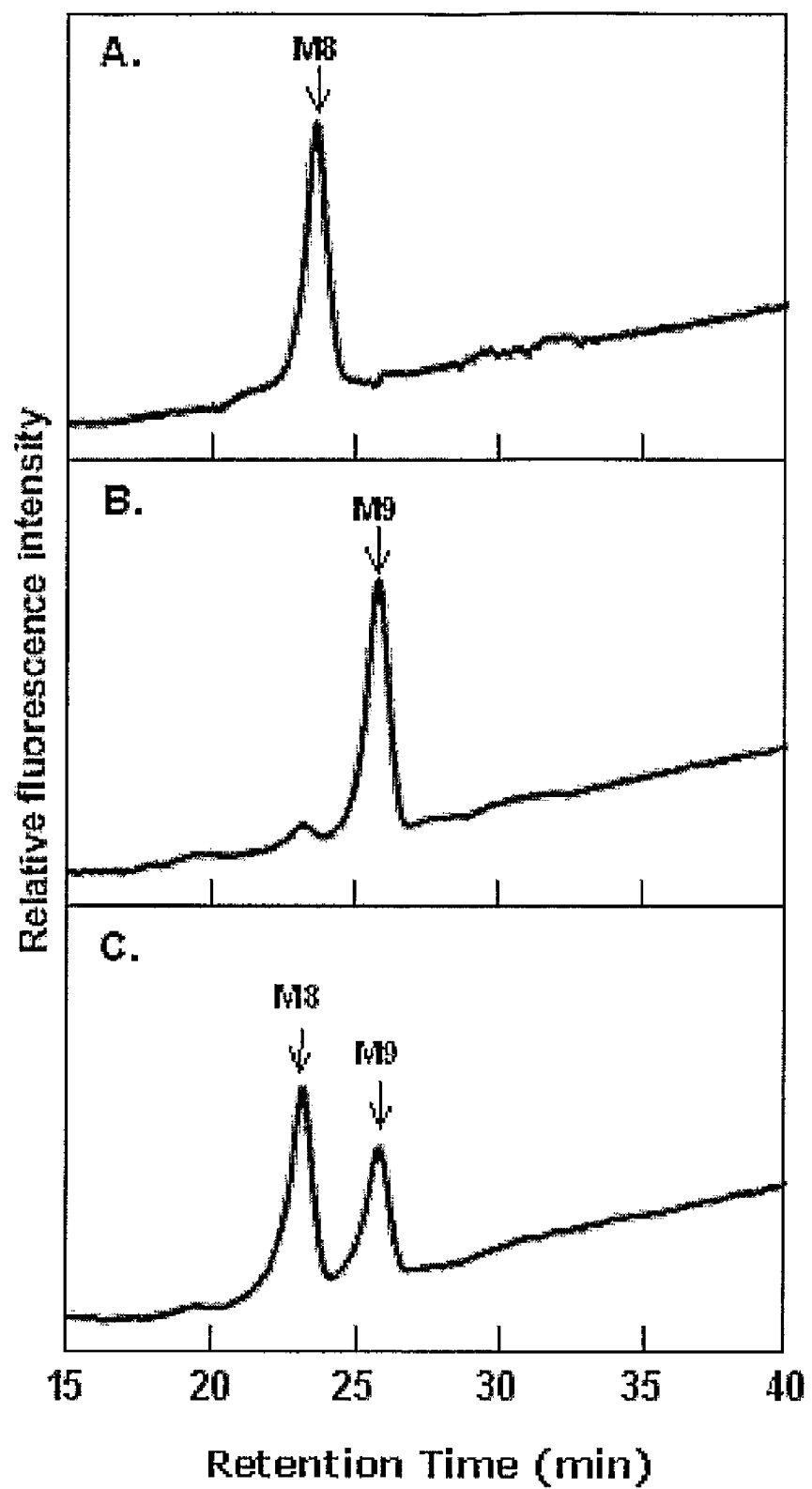
FIG. 7 shows results of tests for measuring α-1,6-mannosyltransferase activity of HpOch2 protein, wherein a *S. cerevisiae* och1Δmnn1Δmnn4Δ mutant strain was transformed with a control vector YEp352GAPII (A), an HpOCH2 gene expression vector YEp352GAPII-HpOCH2 (B) or a ScOCH1 gene expression vector YEp352GAPII-ScOCH1 (C), and membrane fractions obtained from the mutant strain were reacted with $Man_8GlcNAc_2$-PA at 30° C. for two hours and then analyzed by HPLC.

An in vitro assay was performed to determine whether the *H. polymorpha* HpOch2 protein practically has α-1,6-mannosyltransferase activity to add α-1,6-mannose to a core sugar chain like the *S. cerevisiae* Och1 protein. A mutant strain (och1Δmnn1Δmnn4Δ) disrupted in three genes, OCH1, MNN1 and MNN4, has a complete loss of outer chain synthesis (Chiba et al., J. Biol. Chem., 273, 26298-26304, (1998)). The och1Δmnn1Δmnn4Δ mutant was transformed with the *H. polymorpha* HpOCH2 gene expression vector, and a membrane fraction was prepared. The membrane fraction was used as an enzyme source for measuring α-1,6-mannosyltransferase and reacted with a substrate having a core sugar chain structure, $Man_8GlcNAc_2$-PA. The resulting reaction solution was analyzed by HPLC. When the och1Δmnn1Δmnn4Δ mutant was transformed with the Yep352GAPII vector not containing HpOCH2 gene, the concentration of the substrate $Man_8GlcNAc_2$-PA was not changed in a membrane fraction. By contrast, when the och1Δmnn1Δmnn4Δ mutant was transformed respectively with the *H. polymorpha* HpOCH2 gene expression vector and the *S. cerevisiae* OCH1 gene expression vector, a peak corresponding to $Man_9GlcNAc_2$-PA (a structure formed by the addition of a single mannose to $Man_8GlcNAc_2$-PA) was observed in membrane fractions (FIG. 7). These results indicate that the *H. polymorpha* HpOch2 protein, like the *S. cerevisiae* Och1 protein, has the activity of α-1,6-mannosyltransferase involved in the initiation of outer chain elongation.

Example 5

Glycotechnology Using the *H. polymorpha* Hpoch2Δ Mutant

An *H. polymorpha* strain capable of producing a recombinant glycoprotein having a human mannose-type N-linked glycan was established as follows. As described in a previous study (Chiba et al., J. Biol. Chem., 273, 26298-26304, (1998)) carried out with the traditional yeast *Saccharomyces cerevisiae*, the *H. polymorpha* Hpoch2Δ mutant was transfected with a α-1,2-mannosidase expression vector for application to *H. polymorpha*, pDUMOX-MsdS(HA-HDEL), in order to express *Aspergillus saitoi* α-1,2-mannosidase in the ER of *H. polymorpha*, thereby developing a glycoengineered recombinant strain Hpoch2Δ-MsdSp. To construct the α-1,2-mannosidase expression vector, pDUMOX-MsdS(HA-HDEL), PCR was carried out using a plasmid containing *Aspergillus saitoi* α-1,2-mannosidase, pGAMH1 (Chiba et al., J. Biol. Chem., 273, 26298-26304, (1998)), as a template and a forward primer (5"-GGGGAATTCAAAAAAATG-GTGGTCTTCAGCAAA-3': SEQ ID. NO. 13) containing an EcoRI site, and a reverse primer (5'-GGGCCATGGTCA-CAATTCATCATGCGCATAGTCAGGAA-CATCGTATGGGTATGTACTACTC ACCCGCAC-3': SEQ ID. NO. 14) containing an HA sequence for determining protein expression levels, an HDEL (His-Asp-Glu-Leu) sequence as an endoplasmic reticulum retention/retrieval tag and a NcoI site. As a result, the *A. saitoi* α-1,2-mannosidase was amplified, thus yielding a 1.5-kb fragment. The 1.5-kb fragment was digested with EcoRI and NcoI and replaced a GOD gene of a GOD expression vector pDLMOX-GOD(H) (Kim et al. Glycobiology, in press, (2003)). Then, in the resulting GOD expression vector, an *H. polymorpha* LEU2 selection marker was replaced by an *H. polymorpha* URA3 selection marker, thus finally yielding the α-1,2-mannosidase expression vector pDUMOX-MsdS(HA-HDEL). The expression of *A. saitoi* α-1,2-mannosidase in *H. polymorpha* was detected by Western blotting using an anti-HA antibody (Sigma).

Figure 8:
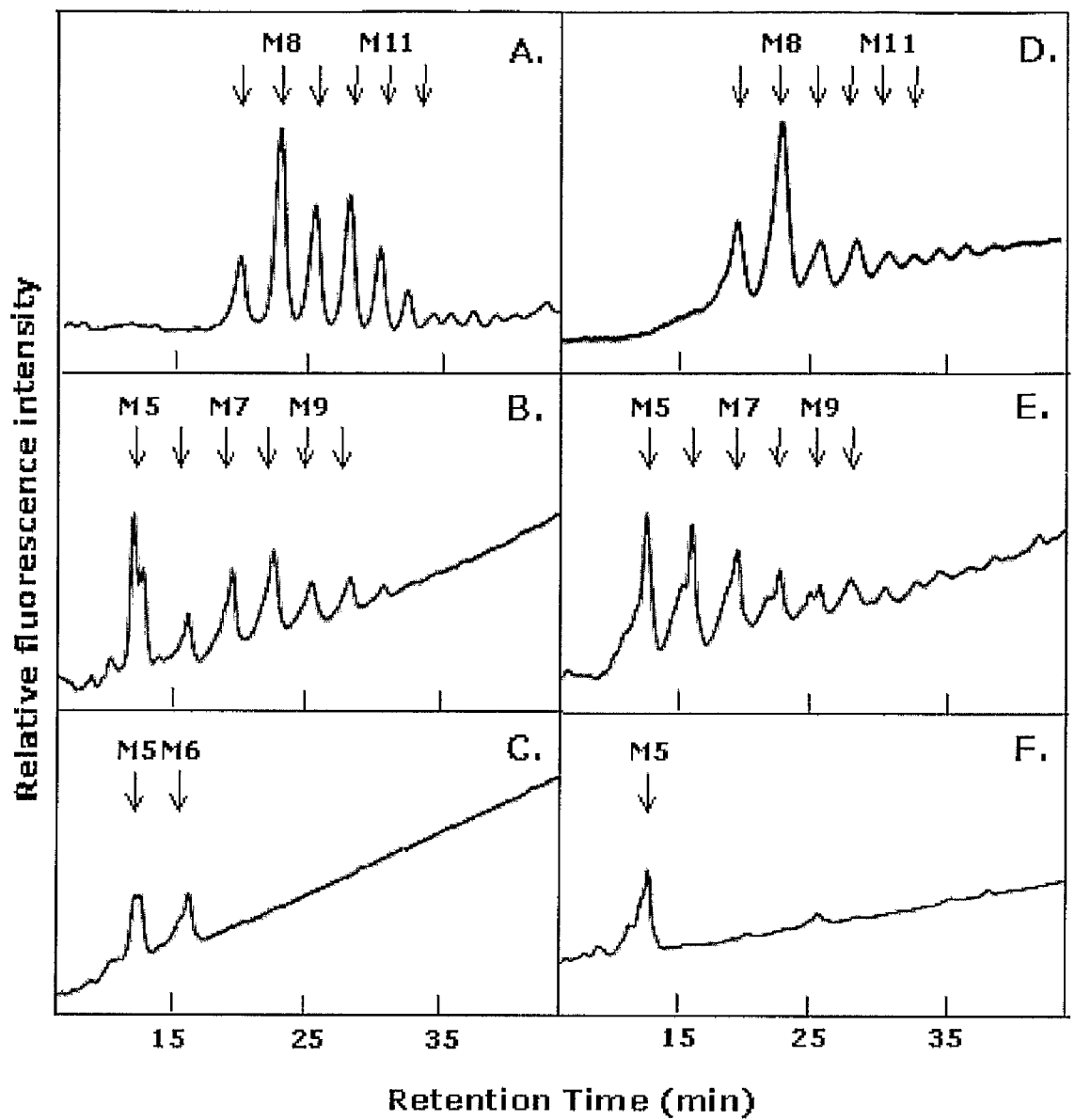
FIG. 8 shows results of HPLC analysis for size distribution and structure of sugar chains attached to GOD expressed in *H. polymorpha* strains (A and D: sugar chain profiles of GOD expressed in a secretory form respectively in a *H. polymorpha* wild type and an Hpoch2Δ mutant; B and E: sugar chain profiles of GOD expressed respectively in a *H. polymorpha* wild type and an Hpoch2Δ mutant which are genetically engineered to express α-1,2-mannosidase derived from *Aspergillus saitoi*; and C and F: sugar chain profiles after treatment with α-1,2-mannosidase for sugar chains respectively from the recombinant wild type and mutant)

To determine whether the glycoengineered *H. polymorpha* strain Hpoch2Δ-MsdSp synthesizes a human mannose-type N-glycan, the structure of sugar chains attached to GOD expressed in a secreted form was analyzed. In a recombinant wild-type strain, HpOCH2-MsdSp, transformed with a heterogeneous α-1,2-mannosidase, sugar chains with 8 or higher mannose residues were sharply reduced, while sugar chains with 5 or 6 mannose residues were increased (the A and B of FIG. 8). In the recombinant Hpoch2Δ-MsdSp strain prepared by transforming the Hpoch2Δ strain with a heterogeneous α-1,2-mannosidase, sugar chains with more than 7 mannose residues were reduced in comparison with the recombinant wild-type strain HpOCH2-MsdSp (the B and E of FIG. 8). When sugar chains isolated from the recombinant wild-type strain and the Hpoch2Δ mutant strain were treated with α-1,2-mannosidase, the sugar chains of the HpOCH2-MsdSp strain were converted to sugar chains with 5 and 6 mannose residues, whereas sugar chains of the Hpoch2Δ-MsdSp strain were converted to sugar chains with 5 mannose residues by α-1,2-mannosidase (the C and F of FIG. 8). These results reveal that, when the heterogeneous α-1,2-mannosidase is introduced into *H. polymorpha*, a wild-type strain still forms yeast-specific α-1,6-mannose linkage by *H. polymorpha* HpOch2 protein, thereby indicating that, to synthesize human mannose-type N-glycans, *H. polymorpha* HpOCH2 gene should be essentially disrupted. Therefore, the Hpoch2Δ mutant strain having a deficient HpOCH2 gene, developed in the present invention, is useful as a host for the production of therapeutic recombinant glycoproteins having human compatible sugar chains. In addition, when various sugar chain-modifying enzymes are expressed in the Hpoch2Δ mutant strain, they come to have various sugar moieties that are not immunogenic in the human body. Thus, the Hpoch2Δ mutant strain is very useful in glycotechnology for the development of a host producing a novel glycoprotein having increased physiological activity as well as having non-immunogenic sugar moieties.

INDUSTRIAL APPLICABILITY

Since *Hansenula polymorpha* has been approved worldwide as a host system for mass production of recombinant hepatitis vaccines, recombinant proteins to be expressed in *H. polymorpha* have a high potential to be developed as biologics. As described in the above Examples, in the Hpoch2Δ mutant strain having a deficiency in *H. polymorpha* HpOCH2 gene, developed in the present invention, the initiation of outer chain elongation is prevented, resulting in the prevention of yeast-specific consecutive α-1,6-mannose addition. Thus, the *H. polymorpha* mutant strain can be used as a host to produce a target glycoprotein in the form of having a sugar chain structure closer to that of human glycoproteins via a secretory pathway. Also, as described above, the Hpoch2Δ mutant strain becomes a basis in glycoengineering for the development of various *H. polymorpha* strains which may be used as hosts for the mass production of recombinant glycoproteins of therapeutic value. Therefore, the present Hpoch2Δ mutant strain is very useful in related industrial fields.

The invention claimed is:

1. An isolated nucleic acid molecule encoding a protein having an amino acid sequence selected from the group consisting of SEQ ID NO. 2 and sequences at least 90% homologous to SEQ ID NO:2, wherein said protein has α-1,6-mannosyltransferase activity, wherein said nucleic acid is obtained from *Hansenula polymorpha*.

2. The isolated nucleic acid molecule according to claim 1, wherein the nucleic acid is designated as SEQ ID NO. 1.

3. An isolated protein which is coded by the nucleic acid of claim 1.

4. A recombinant vector comprising a nucleic acid molecule designated as SEQ ID NO. 1, deposited under accession number KCTC 10583BP.

5. A *Hansenula polymorpha* Hpoch2Δ mutant strain deposited under accession number KCTC 10584BP.

6. The *Hansenula polymorpha* Hpoch2Δ mutant strain according to claim 5, comprising an expression vector for a sugar chain-modifying enzyme.

7. The *Hansenula polymorpha* Hpoch2Δ mutant strain according to claim 6, wherein the sugar chain-modifying enzyme is selected from the group consisting of α-1,2-mannosidase, N-acetyl glucosaminyltransferase I and N-acetyl glucosaminyltransferase II.

8. A process for producing a recombinant glycoprotein in the *Hansenula polymorpha* Hpoch2Δ mutant strain according to claim 5, wherein the recombinant glycoprotein lacks further sugar-chain synthesis of Man$_8$ on N-linked glycosylation.

9. The process according to claim 8, wherein the *Hansenula polymorpha* Hpoch2Δ mutant strain comprises an expression vector for a sugar chain-modifying enzyme, wherein said sugar chain-modifying enzyme is α-1,2-mannosidase.

10. A glycoprotein produced by the process of claim 8 or 9.

11. The *Hansenula polymorpha* Hpoch2Δ mutant strain according to claim 6, wherein the sugar chain-modifying enzyme is α-1,2-mannosidase.

* * * * *

UNITED STATES PATENT AND TRADEMARK OFFICE
CERTIFICATE OF CORRECTION

| | | |
|---|---|---|
| PATENT NO. | : 7,867,730 B2 | Page 1 of 1 |
| APPLICATION NO. | : 10/587956 | |
| DATED | : January 11, 2011 | |
| INVENTOR(S) | : Kang et al. | |

It is certified that error appears in the above-identified patent and that said Letters Patent is hereby corrected as shown below:

On the Title page, at (75), please insert a -- - -- to inventor Joo-Hyung Heo's name.

The CLAIMS in the patent reads:

Column 33, Lines 30-31
CLAIM 4: "A recombinant vector comprising a nucleic acid molecule …"

Column 34, Lines 25-27
CLAIM 8: "…wherein the recombinant glycoprotein lacks further sugar-chain synthesis of Man8 on N-linked glycosylation."

HOWEVER, IT SHOULD READ:

CLAIM 4: "A recombinant vector comprising the nucleic acid molecule…"

CLAIM 8: "…wherein said recombinant glycoprotein further lacks sugar-chain synthesis of Man8 on N-linked glycosylation."

Signed and Sealed this
Fifth Day of April, 2011

David J. Kappos
*Director of the United States Patent and Trademark Office*